United States Patent
Cady

(10) Patent No.: US 10,842,614 B2
(45) Date of Patent: *Nov. 24, 2020

(54) INTRAOCULAR PSEUDOPHAKIC CONTACT LENSES AND RELATED SYSTEMS AND METHODS

(71) Applicant: Kevin J. Cady, St. Charles, IL (US)

(72) Inventor: Kevin J. Cady, St. Charles, IL (US)

(73) Assignee: OnPoint Vision, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/190,959

(22) Filed: Nov. 14, 2018

(65) Prior Publication Data

US 2019/0076237 A1  Mar. 14, 2019

Related U.S. Application Data

(63) Continuation of application No. 14/860,629, filed on Sep. 21, 2015, now Pat. No. 10,159,562.

(Continued)

(51) Int. Cl.
*A61F 2/16* (2006.01)
*A61F 9/00* (2006.01)

(52) U.S. Cl.
CPC .......... *A61F 2/1602* (2013.01); *A61F 2/1648* (2013.01); *A61F 2/1694* (2013.01); *A61F 9/0017* (2013.01);
(Continued)

(58) Field of Classification Search
CPC ................. A61F 2/1602; A61F 2/1694; A61F 2002/16902
(Continued)

(56) References Cited

U.S. PATENT DOCUMENTS 4,124,905 A  11/1978  Clark
5,071,432 A  12/1991  Baikoff
(Continued)

FOREIGN PATENT DOCUMENTS

AU   2014202532 A1   7/2014
BR   PI1005015 A2    4/2013
(Continued)

OTHER PUBLICATIONS

Foreign Communication from Related Counterpart Application; European Patent Application No. 15845158; Extended European Search Report and Written Opinion dated Mar. 6, 2018; 9 pages.
(Continued)

*Primary Examiner* — David H Willse
*Assistant Examiner* — Javier G Blanco

(57) ABSTRACT

Various intraocular pseudophakic contact lenses are disclosed. For example, an intraocular pseudophakic contact lens can include a first optical lens and multiple anchors. The first optical lens is configured to at least partially correct a residual refractive error in an eye. The anchors are configured to be inserted through an anterior surface of an intraocular lens into lens material forming a second optical lens of the intraocular lens in order to secure the intraocular pseudophakic contact lens to the intraocular lens. The anchors can be configured to couple the intraocular pseudophakic contact lens to different types of intraocular lenses, including intraocular lenses not specifically designed to be coupled to or receive the intraocular pseudophakic contact lens. The intraocular pseudophakic contact lens could also include at least one drug-eluting device located on the first optical lens and configured to deliver at least one medication.

20 Claims, 12 Drawing Sheets

Related U.S. Application Data

(60) Provisional application No. 62/053,771, filed on Sep. 22, 2014.

(52) U.S. Cl.
CPC ............... *A61F 2002/1681* (2013.01); *A61F 2002/16902* (2015.04); *A61F 2220/0016* (2013.01)

(58) Field of Classification Search
USPC .................................. 623/6.34, 6.43, 6.46
See application file for complete search history.

(56) References Cited

U.S. PATENT DOCUMENTS

| | | |
|---|---|---|
| 5,078,742 A | 1/1992 | Dahan |
| 5,098,444 A | 3/1992 | Feaster |
| 5,133,747 A | 7/1992 | Feaster |
| 5,201,762 A | 4/1993 | Hauber |
| 5,217,491 A | 6/1993 | Vanderbilt |
| 5,266,241 A | 11/1993 | Parekh |
| 5,275,623 A | 1/1994 | Sarfarazi |
| 5,354,334 A | 10/1994 | Fedorov et al. |
| 5,358,520 A | 10/1994 | Patel |
| 5,443,506 A | 8/1995 | Garabet |
| 5,443,507 A | 8/1995 | Jacobi |
| 5,522,891 A | 6/1996 | Klaas |
| 5,539,016 A | 7/1996 | Kunzler et al. |
| 5,684,560 A | 11/1997 | Roffman et al. |
| 5,693,095 A | 12/1997 | Freeman et al. |
| 5,699,142 A | 12/1997 | Lee et al. |
| 5,728,156 A | 3/1998 | Gupta et al. |
| 5,755,786 A | 5/1998 | Woffinden et al. |
| 5,769,890 A | 6/1998 | McDonald |
| 5,782,911 A | 7/1998 | Herrick |
| 5,824,074 A | 10/1998 | Koch |
| 6,027,531 A | 2/2000 | Tassignon |
| 6,030,416 A | 2/2000 | Huo et al. |
| 6,045,577 A | 4/2000 | Woffinden et al. |
| 6,113,633 A | 9/2000 | Portney |
| 6,142,625 A | 11/2000 | Sawano et al. |
| 6,169,127 B1 | 1/2001 | Lohmann et al. |
| 6,197,057 B1 | 3/2001 | Peyman et al. |
| 6,197,058 B1 | 3/2001 | Portney |
| 6,200,342 B1 | 3/2001 | Tassignon |
| 6,217,171 B1 | 4/2001 | Auten et al. |
| 6,217,612 B1 | 4/2001 | Woods |
| 6,277,146 B1 | 8/2001 | Peyman et al. |
| 6,419,697 B1 | 7/2002 | Kelman |
| 6,454,801 B1 | 9/2002 | Portney |
| 6,464,725 B2 | 10/2002 | Skotton |
| 6,488,708 B2 | 12/2002 | Sarfarazi |
| 6,554,859 B1 | 4/2003 | Lang et al. |
| 6,554,860 B2 | 4/2003 | Hoffmann et al. |
| 6,558,420 B2 | 5/2003 | Green |
| 6,582,076 B1 | 6/2003 | Roffman et al. |
| 6,616,691 B1 | 9/2003 | Tran |
| 6,616,692 B1 | 9/2003 | Glick et al. |
| 6,645,246 B1 | 11/2003 | Weinschenk, III et al. |
| 6,705,729 B2 | 3/2004 | Piers et al. |
| 6,749,634 B2 | 6/2004 | Hanna |
| 6,767,363 B1 | 7/2004 | Bandhauer et al. |
| 6,797,004 B1 | 9/2004 | Brady et al. |
| 6,818,017 B1 | 11/2004 | Shu |
| 6,827,738 B2 | 12/2004 | Willis et al. |
| 6,851,803 B2 | 2/2005 | Wooley et al. |
| 6,860,601 B2 | 3/2005 | Shadduck |
| 6,880,558 B2 | 4/2005 | Perez |
| 6,926,736 B2 | 8/2005 | Peng et al. |
| 6,952,313 B2 | 10/2005 | Schrader |
| 6,960,230 B2 | 11/2005 | Haefliger |
| 6,960,231 B2 | 11/2005 | Tran |
| 6,991,651 B2 | 1/2006 | Portney |
| 7,008,448 B2 | 3/2006 | Lipshitz et al. |
| 7,036,931 B2 | 5/2006 | Lindacher et al. |
| 7,111,938 B2 | 9/2006 | Andino et al. |
| 7,118,597 B2 | 10/2006 | Miller et al. |
| 7,150,760 B2 | 12/2006 | Zhang |
| 7,186,266 B2 | 3/2007 | Peyman |
| 7,223,288 B2 | 5/2007 | Zhang et al. |
| 7,238,201 B2 | 7/2007 | Portney et al. |
| 7,279,006 B2 | 10/2007 | Vincent |
| 7,311,194 B2 | 12/2007 | Jin et al. |
| 7,316,713 B2 | 1/2008 | Zhang |
| 7,338,161 B2 | 3/2008 | Chauveau et al. |
| 7,452,378 B2 | 11/2008 | Zadno-Azizi et al. |
| 7,453,646 B2 | 11/2008 | Lo |
| 7,462,193 B2 | 12/2008 | Nagamoto |
| 7,572,007 B2 | 8/2009 | Simpson |
| 7,591,849 B2 | 9/2009 | Richardson |
| 7,604,349 B2 | 10/2009 | Blum et al. |
| 7,794,498 B2 | 9/2010 | Pinchuk |
| 7,842,087 B2 | 11/2010 | Ben Nun |
| 7,871,162 B2 | 1/2011 | Weeber |
| 7,871,437 B2 | 1/2011 | Hermans et al. |
| 7,875,661 B2 | 1/2011 | Salamone |
| 7,892,284 B2 | 2/2011 | Iwamoto |
| 7,905,917 B2 | 3/2011 | Altmann |
| 7,918,886 B2 | 4/2011 | Aharoni et al. |
| 7,942,929 B2 | 5/2011 | Linhardt et al. |
| 7,955,704 B2 | 6/2011 | Lowery et al. |
| 8,012,204 B2 | 9/2011 | Weinschenk, III et al. |
| 8,034,107 B2 | 10/2011 | Stenger |
| 8,109,999 B2 | 2/2012 | Hampp |
| 8,133,274 B2 | 3/2012 | Zhou et al. |
| 8,197,541 B2 | 6/2012 | Schedler |
| 8,231,219 B2 | 7/2012 | Weeber |
| 8,273,123 B2 | 9/2012 | Ben Nun |
| 8,324,256 B2 | 12/2012 | Domschke et al. |
| 8,337,552 B2 | 12/2012 | Kobayashi et al. |
| 8,377,124 B2 | 2/2013 | Hong et al. |
| 8,419,791 B2 | 4/2013 | Toop |
| 8,430,928 B2 | 4/2013 | Liao |
| 8,491,661 B2 | 7/2013 | Mouillet et al. |
| 8,523,942 B2 | 9/2013 | Cumming |
| 8,530,590 B2 | 9/2013 | Hu et al. |
| 8,579,972 B2 | 11/2013 | Rombach |
| 8,603,167 B2 | 12/2013 | Rombach |
| 8,608,799 B2 | 12/2013 | Blake |
| 8,636,358 B2 | 1/2014 | Binder |
| 8,680,172 B2 | 3/2014 | Liao |
| 8,696,746 B2 | 4/2014 | Wanders et al. |
| 8,834,566 B1 | 9/2014 | Jones |
| 8,852,274 B2 | 10/2014 | Doraiswamy et al. |
| 8,858,626 B2 | 10/2014 | Noy |
| 8,920,495 B2 | 12/2014 | Mirlay |
| 8,945,213 B2 | 2/2015 | Terwee et al. |
| 8,992,611 B2 | 3/2015 | Zhao |
| 8,968,399 B2 | 5/2015 | Ghabra |
| 9,072,600 B2 | 7/2015 | Tran |
| 9,084,674 B2 | 7/2015 | Brady et al. |
| 9,237,946 B2 | 1/2016 | Pynson |
| 9,304,329 B2 | 4/2016 | Zhao |
| 9,329,410 B2 | 5/2016 | Riall et al. |
| 9,554,893 B2 | 1/2017 | Brady et al. |
| 9,675,445 B2 | 6/2017 | Moriarty |
| 9,757,228 B2 | 9/2017 | Wanders et al. |
| 9,820,849 B2 | 11/2017 | Jansen |
| 9,869,885 B2 | 1/2018 | De Sio et al. |
| 2002/0120329 A1 | 8/2002 | Lang et al. |
| 2002/0161436 A1 | 10/2002 | Portney |
| 2003/0158560 A1 | 8/2003 | Portney |
| 2003/0187504 A1 | 10/2003 | Weinschenk, III et al. |
| 2003/0220687 A1 | 11/2003 | Nordan et al. |
| 2004/0106993 A1 | 6/2004 | Portney |
| 2004/0158322 A1 | 8/2004 | Shen |
| 2004/0167621 A1 | 8/2004 | Peyman |
| 2004/0249455 A1 | 12/2004 | Tran |
| 2005/0027354 A1 | 2/2005 | Brady et al. |
| 2005/0060032 A1 | 3/2005 | Magnante et al. |
| 2005/0113913 A1 | 5/2005 | Duvert |
| 2006/0001186 A1 | 1/2006 | Richardson et al. |
| 2006/0142856 A1 | 6/2006 | Willis et al. |
| 2006/0184244 A1 | 8/2006 | Nguyen et al. |

(56) References Cited

U.S. PATENT DOCUMENTS

| | | |
|---|---|---|
| 2006/0241752 A1 | 10/2006 | Israel |
| 2006/0253196 A1 | 11/2006 | Woods |
| 2006/0265059 A1 | 11/2006 | Sunada et al. |
| 2007/0010881 A1 | 1/2007 | Soye et al. |
| 2007/0016293 A1 | 1/2007 | Tran |
| 2007/0032866 A1 | 2/2007 | Portney |
| 2007/0118216 A1 | 5/2007 | Pynson |
| 2007/0260308 A1 | 11/2007 | Tran |
| 2007/0270947 A1 | 11/2007 | Peyman |
| 2007/0282438 A1 | 12/2007 | Hong et al. |
| 2008/0051886 A1 | 2/2008 | Lin |
| 2008/0086208 A1 | 4/2008 | Nordan |
| 2008/0103592 A1 | 5/2008 | Maloney |
| 2008/0147085 A1 | 6/2008 | Gardeski et al. |
| 2008/0208334 A1 | 8/2008 | Jinkerson et al. |
| 2008/0208335 A1 | 8/2008 | Blum |
| 2008/0281414 A1 | 11/2008 | Akahoshi |
| 2008/0288066 A1 | 11/2008 | Cumming |
| 2008/0312738 A1 | 12/2008 | Wanders |
| 2009/0048671 A1 | 2/2009 | Lipshitz et al. |
| 2009/0062911 A1 | 3/2009 | Bogaert |
| 2009/0130176 A1 | 5/2009 | Bossy-Nobs et al. |
| 2009/0182422 A1 | 7/2009 | Nordan et al. |
| 2009/0198326 A1 | 8/2009 | Zhou et al. |
| 2010/0004742 A1 | 1/2010 | Cumming |
| 2010/0016965 A1 | 1/2010 | Hong et al. |
| 2010/0036488 A1 | 2/2010 | de Juan, Jr. et al. |
| 2010/0094412 A1 | 4/2010 | Wensrich |
| 2010/0094413 A1 | 4/2010 | Rombach et al. |
| 2010/0280609 A1 | 11/2010 | Simonov et al. |
| 2010/0292789 A1 | 11/2010 | Willis et al. |
| 2011/0021733 A1 | 1/2011 | Wanders et al. |
| 2011/0153014 A1 | 6/2011 | Zhang et al. |
| 2011/0313520 A1 | 12/2011 | Shoji et al. |
| 2011/0313521 A1 | 12/2011 | Angelopoulos |
| 2011/0313522 A1 | 12/2011 | Hayes |
| 2011/0313523 A1 | 12/2011 | Hayes |
| 2012/0109294 A1 | 5/2012 | Olson |
| 2012/0232649 A1 | 9/2012 | Cuevas |
| 2012/0253459 A1 | 10/2012 | Reich et al. |
| 2012/0323321 A1 | 12/2012 | Simonov et al. |
| 2013/0066422 A1 | 3/2013 | Dworschak et al. |
| 2013/0110234 A1 | 5/2013 | DeVita et al. |
| 2013/0110235 A1 | 5/2013 | Schwiegerling |
| 2013/0131796 A1 | 5/2013 | Mirlay |
| 2013/0190868 A1 | 7/2013 | Kahook et al. |
| 2013/0197636 A1 | 8/2013 | Haefliger |
| 2013/0204364 A1 | 8/2013 | Olson |
| 2013/0238091 A1 | 9/2013 | Danta et al. |
| 2013/0253159 A1 | 9/2013 | Benz et al. |
| 2013/0317607 A1 | 11/2013 | DeBoer et al. |
| 2013/0338767 A1 | 12/2013 | Mazzocchi et al. |
| 2014/0052246 A1 | 2/2014 | Kahook et al. |
| 2014/0121768 A1 | 5/2014 | Simpson |
| 2014/0180406 A1 | 6/2014 | Simpson |
| 2014/0228949 A1 | 8/2014 | Argento et al. |
| 2014/0240657 A1 | 8/2014 | Pugh et al. |
| 2014/0243972 A1 | 8/2014 | Wanders |
| 2014/0253877 A1 | 8/2014 | Li et al. |
| 2014/0330375 A1 | 11/2014 | McCafferty |
| 2014/0330376 A1 | 11/2014 | Kleinman |
| 2014/0347624 A1 | 11/2014 | Ando et al. |
| 2014/0368789 A1 | 12/2014 | Webb |
| 2015/0230981 A1 | 8/2015 | Kahook et al. |
| 2016/0008126 A1 | 1/2016 | Salahieh et al. |
| 2016/0317286 A1 | 11/2016 | Brady et al. |

FOREIGN PATENT DOCUMENTS

| | | |
|---|---|---|
| BR | 102012000755 A2 | 10/2013 |
| CN | 2717403 Y | 8/2005 |
| CN | 201015617 Y | 2/2008 |
| CN | 203425064 U | 2/2014 |
| DE | 19501444 A1 | 7/1996 |
| DE | 20109306 U1 | 8/2001 |
| DE | 10025320 A1 | 11/2001 |
| DE | 202010002895 U1 | 5/2010 |
| DE | 202013009162 U1 | 11/2013 |
| EP | 0760232 A1 | 3/1997 |
| EP | 1369710 A2 | 12/2003 |
| EP | 1449498 A2 | 8/2004 |
| EP | 1493405 A1 | 1/2005 |
| EP | 1504730 A1 | 2/2005 |
| EP | 1658828 A1 | 5/2006 |
| FR | 2666735 A1 | 3/1992 |
| FR | 2869793 A1 | 11/2005 |
| FR | 2998474 A1 | 5/2014 |
| GB | 2464505 A | 4/2010 |
| GB | 2517531 A | 2/2015 |
| JP | H07255757 A | 10/1995 |
| JP | 4199573 B2 | 10/2004 |
| JP | 4363573 B2 | 11/2009 |
| JP | 4431372 B2 | 3/2010 |
| JP | 5398089 B2 | 6/2013 |
| JP | 5383782 B2 | 1/2014 |
| RU | 2045246 C1 | 10/1995 |
| RU | 2080100 C1 | 8/1996 |
| RU | 2070004 C1 | 12/1996 |
| RU | 2129880 C1 | 5/1999 |
| RU | 2134086 C1 | 8/1999 |
| RU | 31954 U1 | 9/2003 |
| RU | 2234417 C2 | 8/2004 |
| RU | 47696 U1 | 9/2005 |
| RU | 2281063 C1 | 8/2006 |
| RU | 2281067 C1 | 8/2006 |
| RU | 2281726 C1 | 8/2006 |
| RU | 2283067 C1 | 9/2006 |
| RU | 2288494 C2 | 11/2006 |
| RU | 2377964 C2 | 1/2010 |
| RU | 2457811 C1 | 8/2012 |
| RU | 2479286 C1 | 4/2013 |
| RU | 2531472 C1 | 10/2014 |
| TW | M329428 U | 4/2008 |
| TW | 201103517 A | 2/2011 |
| WO | 91/13597 A1 | 9/1991 |
| WO | 92/15260 A1 | 9/1992 |
| WO | 94/07435 A1 | 4/1994 |
| WO | 94/13225 A1 | 6/1994 |
| WO | 96/05047 A1 | 2/1996 |
| WO | 97/12564 A1 | 4/1997 |
| WO | 99/18457 A2 | 4/1999 |
| WO | 99/35520 A1 | 7/1999 |
| WO | 99/56671 A1 | 11/1999 |
| WO | 99/62434 A1 | 12/1999 |
| WO | 00/48491 A1 | 8/2000 |
| WO | 01/08605 A1 | 2/2001 |
| WO | 01/15635 A1 | 3/2001 |
| WO | 01/87182 A2 | 11/2001 |
| WO | 2005/104994 A2 | 11/2005 |
| WO | 2006/025726 A1 | 3/2006 |
| WO | 2006/119016 A2 | 11/2006 |
| WO | 2007/138564 A1 | 12/2007 |
| WO | 2008/094518 A1 | 8/2008 |
| WO | 2010/131955 A1 | 11/2010 |
| WO | 2011/115860 A2 | 9/2011 |
| WO | 2013/055212 A1 | 4/2013 |
| WO | 2013/169652 A2 | 11/2013 |
| WO | 2014/058315 A1 | 4/2014 |
| WO | 2014/058316 A1 | 4/2014 |
| WO | 2014/071532 A1 | 5/2014 |
| WO | 2014/099338 A1 | 6/2014 |
| WO | 2014/108100 A1 | 7/2014 |
| WO | 2015/006839 A1 | 1/2015 |
| WO | 2015/022514 A1 | 2/2015 |
| WO | 2015026226 A1 | 2/2015 |
| WO | 2015/037994 A1 | 3/2015 |
| WO | 2015/044235 A1 | 4/2015 |
| WO | 2015/066502 A1 | 5/2015 |

OTHER PUBLICATIONS

Office Action dated Aug. 1, 2019 in connection with Japanese Patent Application No. 2017-535622, 11 pages.

(56) References Cited

OTHER PUBLICATIONS

Office Action dated Jun. 24, 2019 in connection with New Zealand Patent Application No. 729994, 3 pages.
Office Action in connection with Australian Patent Application No. 2019204613 dated Nov. 22, 2019, 3 pages.
Examination Report dated Apr. 5, 2019 in connection with Australian Patent Application No. 2015321522, 4 pages.

INTRAOCULAR PSEUDOPHAKIC CONTACT LENSES AND RELATED SYSTEMS AND METHODS

CROSS-REFERENCE TO RELATED APPLICATIONS AND PRIORITY CLAIM

This application is a continuation of U.S. patent application Ser. No. 14/860,629 filed on Sep. 21, 2015, which claims priority under 35 U.S.C. § 119(e) to U.S. Provisional Patent Application No. 62/053,771 filed on Sep. 22, 2014. These applications are hereby incorporated by reference in their entirety.

TECHNICAL FIELD

This disclosure relates generally to implantable optical devices. More specifically, this disclosure relates to intraocular pseudophakic contact lenses and related systems and methods.

BACKGROUND

In a normal human eye, light enters through the cornea and passes through the pupil, and the natural crystalline lens focuses the light onto the retina of the eye. However, due to cataracts or other problems, the natural crystalline lens of an eye may need to be replaced with an artificial intraocular lens (IOL). The term "pseudophakia" is used to describe an eye in which the natural crystalline lens has been replaced with an intraocular lens.

Before an intraocular lens is placed into a patient's eye, a doctor or other personnel typically selects an intraocular lens that is designed to provide desired refractive correction for the patient's eye. For example, an intraocular lens could have an optical lens designed to correct myopia (near-sightedness), hyperopia (far-sightedness), astigmatism, or other refractive errors that occur naturally in the patient's eye. However, it is often the case that the intraocular lens selected for a patient's eye does not fully correct (and may even cause) some form of refractive error in the patient's eye. This refractive error is referred to as "residual" refractive error.

There are various conventional options for correcting residual refractive error, all of which have their disadvantages. For example, one intraocular lens in a patient's eye could be replaced with a different intraocular lens, but this typically has a high risk of surgical complications. Ablation surgery (such as LASIK) on the cornea of a patient's eye could be done to correct residual refractive error, but this can have a high level of unwanted side effects, particularly for older patients. An additional intraocular lens (often referred to as a "piggyback" IOL) could be inserted in front of an existing intraocular lens, but this is typically an invasive procedure with less predictability associated with the final refractive outcome. In addition, intracorneal lenses (ICLs) can be inserted into the cornea of a patient's eye, but this is often more invasive and has a high degree of rejection. In general, the above procedures are typically not predictable and have a higher degree of surgical risk. Also, the devices used in the above procedures are difficult to remove and "reverse" any residual refractive error, resulting in a higher risk of leaving the patient with induced visual aberration.

SUMMARY

This disclosure relates to intraocular pseudophakic contact lenses and related systems and methods.

In a first embodiment, an apparatus includes an intraocular pseudophakic contact lens. The intraocular pseudophakic contact lens includes a first optical lens configured to at least partially correct a residual refractive error in an eye, where the residual refractive error includes a refractive error that exists in the eye after implantation of an artificial intraocular lens in the eye. The intraocular pseudophakic contact lens also includes multiple anchors configured to be inserted through an anterior surface of the artificial intraocular lens into lens material forming a second optical lens of the artificial intraocular lens in order to secure the intraocular pseudophakic contact lens to the artificial intraocular lens. The intraocular pseudophakic contact lens further includes multiple projections including extensions of the first optical lens such that the first optical lens and the projections include a common material, where the anchors are partially embedded in or are configured to pass through the extensions of the first optical lens. The artificial intraocular lens lacks predefined openings that receive the anchors. The anchors are configured to pierce the lens material forming the second optical lens of the artificial intraocular lens in order to secure the intraocular pseudophakic contact lens to the artificial intraocular lens. The anchors include substantially straight pins extending axially along an optical axis of the intraocular pseudophakic contact lens away from the first optical lens.

In a second embodiment, a system includes an intraocular pseudophakic contact lens including a first optical lens configured to at least partially correct a residual refractive error in an eye, multiple anchors, and multiple projections including extensions of the first optical lens such that the first optical lens and the projections include a common material. The anchors are partially embedded in or are configured to pass through the extensions of the first optical lens. The system also includes an artificial intraocular lens including a second optical lens, where the second optical lens is formed of lens material. The anchors are configured to be inserted through an anterior surface of the artificial intraocular lens into the lens material in order to secure the intraocular pseudophakic contact lens to the artificial intraocular lens. The artificial intraocular lens lacks predefined openings that receive the anchors. The anchors are configured to pierce the lens material forming the second optical lens of the artificial intraocular lens in order to secure the intraocular pseudophakic contact lens to the artificial intraocular lens. The anchors include substantially straight pins extending axially along an optical axis of the intraocular pseudophakic contact lens away from the first optical lens.

In a third embodiment, a method includes coupling an intraocular pseudophakic contact lens to an artificial intraocular lens. The intraocular pseudophakic contact lens includes a first optical lens configured to at least partially correct a residual refractive error in an eye, multiple anchors, and multiple projections including extensions of the first optical lens such that the first optical lens and the projections include a common material. The anchors are partially embedded in or are configured to pass through the extensions of the first optical lens. Coupling the intraocular pseudophakic contact lens to the artificial intraocular lens includes inserting the multiple anchors through an anterior surface of the artificial intraocular lens into lens material forming a second optical lens of the artificial intraocular lens in order to secure the intraocular pseudophakic contact lens to the artificial intraocular lens. The artificial intraocular lens lacks predefined openings that receive the anchors. The anchors are configured to pierce the lens material forming the second optical lens of the artificial intraocular lens in order to secure the intraocular pseudophakic contact lens to the artificial intraocular lens. The anchors include substantially straight pins extending axially along an optical axis of the intraocular pseudophakic contact lens away from the first optical lens.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 25, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

This disclosure provides various intraocular pseudophakic contact lenses (IOPCLs) that can be used in conjunction with intraocular lenses (IOLs). An intraocular pseudophakic contact lens generally represents a contact lens-type device that can be implanted within a patient's eye and placed on the anterior surface of an intraocular lens in the patient's eye. The intraocular pseudophakic contact lens substantially corrects residual refractive error present after implantation of the intraocular lens, such as after a lensectomy (cataract) procedure.

Unlike conventional approaches, an intraocular pseudophakic contact lens can be implanted with less surgical risk. Moreover, an intraocular pseudophakic contact lens allows a patient to see immediately after implantation of the intraocular pseudophakic contact lens. Further, an intraocular pseudophakic contact lens can be easily replaced if a different lens is needed to correct residual refractive error or even removed if necessary. In addition, with techniques such as intraoperative wavefront aberrometry now available, refractive outcome can be measured during the actual procedure in which an intraocular pseudophakic contact lens is being implanted, which helps to identify immediately that a desired refractive target is obtained.

Figure 1:
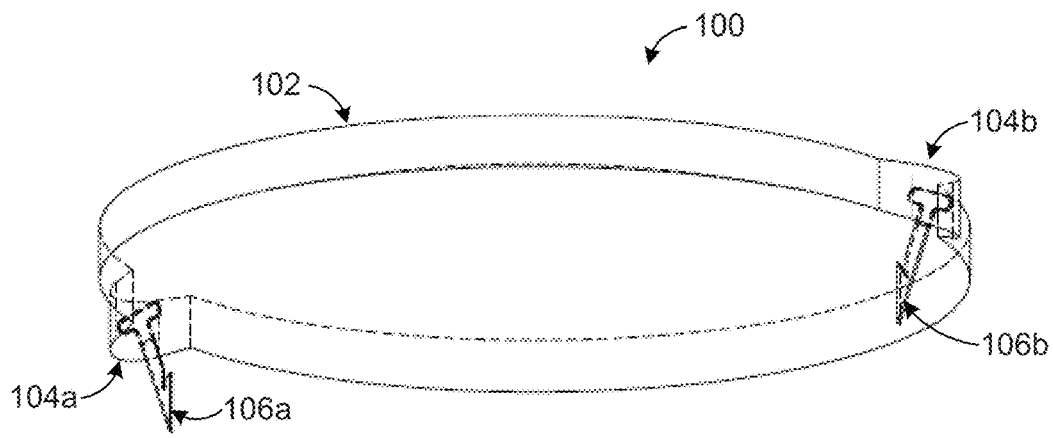
FIGS. 1 through 3 illustrate a first example intraocular pseudophakic contact lens (IOPCL) according to this disclosure.
Figure 2:
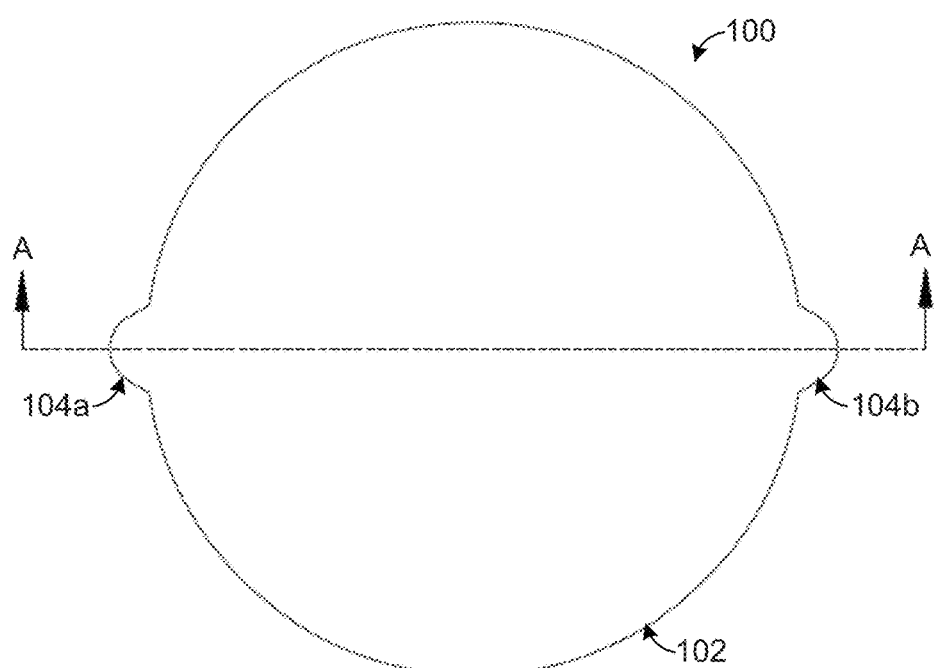
Figure 3:
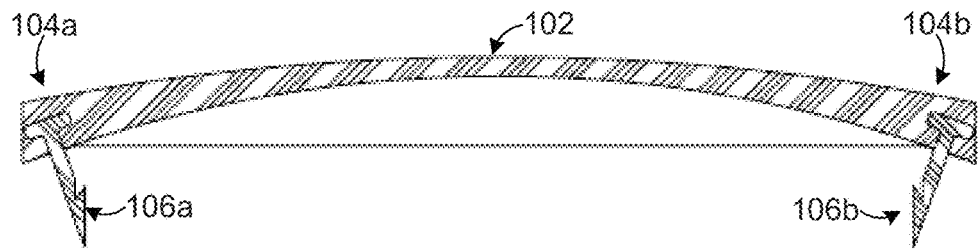

FIGS. 1 through 3 illustrate a first example intraocular pseudophakic contact lens (IOPCL) 100 according to this disclosure. In particular, FIG. 1 illustrates an oblique view of the intraocular pseudophakic contact lens 100, FIG. 2 illustrates a top view of the intraocular pseudophakic contact lens 100, and FIG. 3 illustrates a cut-away view of the intraocular pseudophakic contact lens 100 along line A-A in FIG. 2.

As shown in FIGS. 1 through 3, the intraocular pseudophakic contact lens 100 includes an optical lens 102. The optical lens 102 denotes the portion of the intraocular pseudophakic contact lens 100 that alters light passing through the intraocular pseudophakic contact lens 100. The light that passes through the optical lens 102 then travels through an associated intraocular lens before reaching the retina of a patient's eye.

The optical lens 102 can be formed from any suitable material(s), such as silicone or acrylic. The optical lens 102 can also be formed in any suitable manner, such as by using a mold or lathe cut manufacturing process. Different lenses 102 can be designed and manufactured to provide a wide range of diopters, and each optical lens 102 can be designed to correct any suitable refractive error(s). Example types of refractive errors that can be corrected include myopia, hyperopia, and astigmatism.

The optical lens 102 in this example has a convex top surface and a concave bottom surface. However, the optical lens 102 can have any other suitable shape, which could depend (at least in part) on the type of refractive error(s) being corrected. As particular examples, the optical lens 102 could be convex, concave, spherical, aspherical, toric, mono-focal, or multi-focal. The specific lens platform used as the optical lens 102 in the intraocular pseudophakic contact lens 100 can be selected to provide the desired refractive correction in a patient's eye. The optical lens 102 could also include various other features as needed or desired, such as when the optical lens 102 is weighted (like at its bottom) so that the optical lens 102 orients itself on an intraocular lens in a desired orientation (like for toric platforms) or when the optical lens 102 is tinted, is photochromic, or includes an ultraviolet (UV) absorber.

Multiple projections 104a-104b extend from multiple sides of the optical lens 102. The projections 104a-104b are used to retain multiple anchors 106a-106b that extend below the intraocular pseudophakic contact lens 100. Each projection 104a-104b could be formed from any suitable material(s) and in any suitable manner. For example, the projections 104a-104b could represent portions of the material(s) forming the optical lens 102 and therefore represent extensions of the optical lens 102 itself. However, this need not be the case. For instance, the optical lens 102 could be placed within a retaining ring that is integral with or attached to the projections 104a-104b, or the projections 104a-104b could be secured to the optical lens 102 itself using adhesive or other suitable connecting mechanism. Note that while two projections 104a-104b are shown here, the intraocular pseudophakic contact lens 100 could include any number of projections, including a single projection.

The anchors 106a-106b are used to secure the intraocular pseudophakic contact lens 100 to an intraocular lens. For example, after the intraocular pseudophakic contact lens 100 is inserted into a patient's eye, a surgeon or other personnel could push the projections 104a-104b or other portion(s) of the intraocular pseudophakic contact lens 100 down onto an intraocular lens. This drives the anchors 106a-106b through the anterior (front) surface of the intraocular lens and helps to secure the intraocular pseudophakic contact lens 100 to the intraocular lens. Each anchor 106a-106b represents any suitable structure for securing an intraocular pseudophakic contact lens to an intraocular lens. In this example, the anchors 106a-106b represent barbed or ribbed pins, although other types of anchors could also be used, such as screw picks. Each anchor 106a-106b could be formed from any suitable material(s) and in any suitable manner. Note that while two anchors 106a-106b are shown here, the intraocular pseudophakic contact lens 100 could include any number of anchors, including a single anchor.

In the intraocular pseudophakic contact lens 100 of FIGS. 1 through 3, the anchors 106a-106b can be permanently embedded in the projections 104a-104b of the intraocular pseudophakic contact lens 100. However, this need not be the case.

Figure 4:
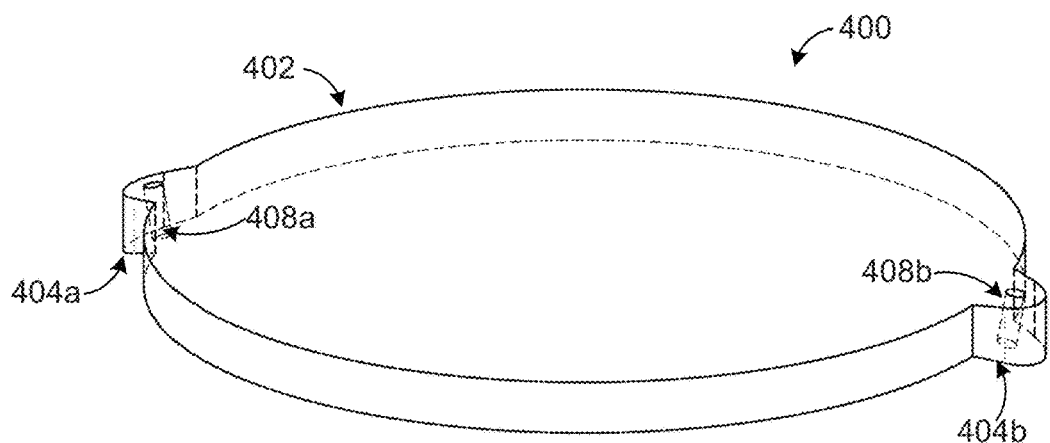
FIGS. 4 through 7 illustrate a second example intraocular pseudophakic contact lens according to this disclosure.
Figure 5:
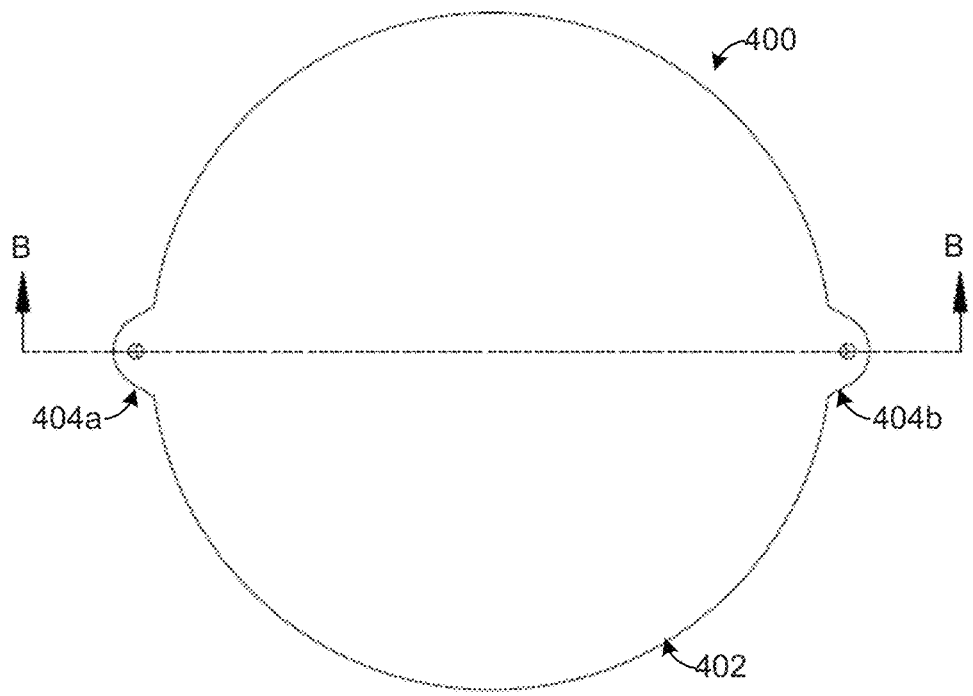
Figure 6:
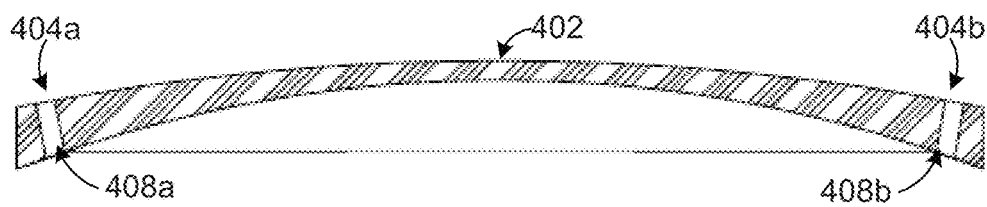
Figure 7:
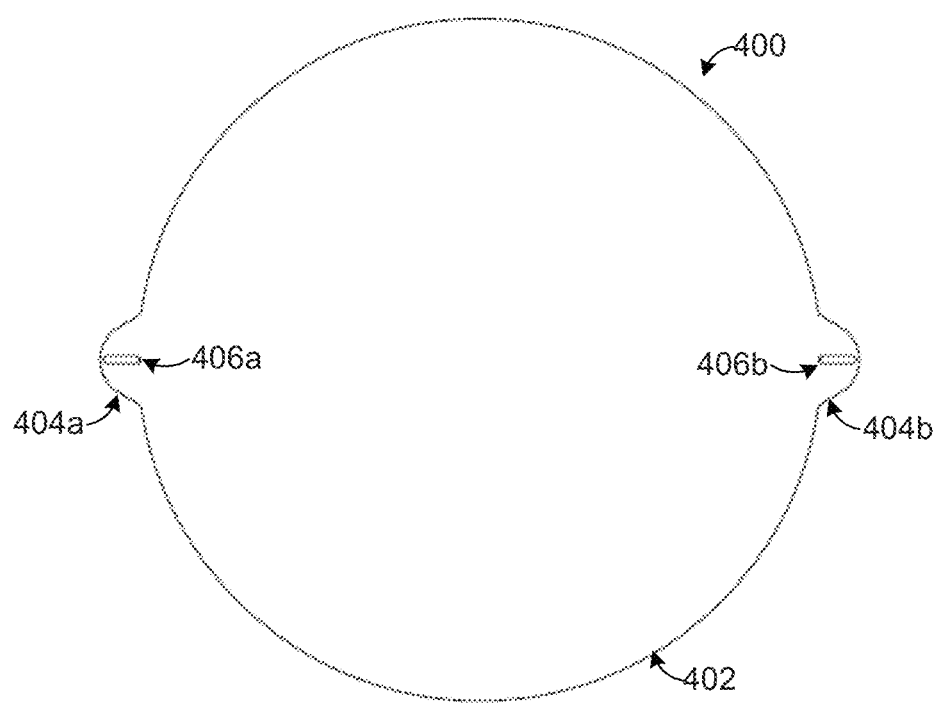

FIGS. 4 through 7 illustrate a second example intraocular pseudophakic contact lens 400 according to this disclosure. In particular, FIG. 4 illustrates an oblique view of the intraocular pseudophakic contact lens 400, and FIG. 5 illustrates a top view of the intraocular pseudophakic contact lens 400. Also, FIG. 6 illustrates a cut-away view of the intraocular pseudophakic contact lens 400 along line B-B in FIG. 5, and FIG. 7 illustrates a bottom view of the intraocular pseudophakic contact lens 400.

As shown in FIGS. 4 through 7, the intraocular pseudophakic contact lens 400 has various components that are the same as or similar to those forming the intraocular pseudophakic contact lens 100. For example, the intraocular pseudophakic contact lens 400 includes an optical lens 402 and multiple projections 404a-404b. Also, the intraocular pseudophakic contact lens 400 is secured to an intraocular lens using multiple anchors 406a-406b. However, the intraocular pseudophakic contact lens 400 here includes holes 408a-408b formed through the projections 404a-404b, and the anchors 406a-406b are inserted through the holes 408a-408b.

The optical lens 402 can be formed from any suitable material(s), such as silicone or acrylic. The optical lens 402 can also be formed in any suitable manner, such as by using a mold or lathe cut manufacturing process. Different lenses 402 can be designed and manufactured to provide a wide range of diopters, and each optical lens 402 can be designed to correct any suitable refractive error(s). While the optical lens 402 in this example has a convex top surface and a concave bottom surface, the optical lens 402 can have any other suitable shape, which could depend (at least in part) on the type of refractive error(s) being corrected. As particular examples, the optical lens 402 could be convex, concave, spherical, aspherical, toric, mono-focal, or multi-focal. The specific lens platform used as the optical lens 402 in the intraocular pseudophakic contact lens 400 can be selected to provide the desired refractive correction in a patient's eye. The optical lens 402 could also include various other features as needed or desired, such as when the optical lens 402 is weighted (like at its bottom) so that the optical lens 402 orients itself on an intraocular lens in a desired orientation (like for toric platforms) or when the optical lens 402 is tinted, is photochromic, or includes an ultraviolet (UV) absorber.

Each projection 404a-404b could be formed from any suitable material(s) and in any suitable manner. For example, the projections 404a-404b could represent portions of the material(s) forming the optical lens 402 and therefore represent extensions of the optical lens 402 itself. However, this need not be the case. For instance, the optical lens 402 could be placed within a retaining ring that is integral with or attached to the projections 404a-404b, or the projections 404a-404b could be secured to the optical lens 402 itself using adhesive or other suitable connecting mechanism.

Each anchor 406a-406b represents any suitable structure for securing an intraocular pseudophakic contact lens to an intraocular lens. In this example, the anchors 406a-406b represent barbed or ribbed pins, although other types of anchors could also be used, such as screw picks. Each anchor 406a-406b could be formed from any suitable material(s) and in any suitable manner.

Each hole 408a-408b could have any suitable size, shape, and dimensions. Also, each hole 408a-408b could be formed in any suitable manner. For example, in some embodiments, a hole 408a-408b could be formed through an associated projection 404a-404b after the projection 404a-404b is formed, such as by using a mechanical or laser drill. In other embodiments, each projection 404a-404b could be formed already including the associated hole 408a-408b.

Note that while two projections 404a-404b, two anchors 406a-406b, and two holes 408a-408b are shown here, the intraocular pseudophakic contact lens 400 could include any number of projections, anchors, and holes. Also, while each projection 404a-404b is shown as including a single cylindrical hole 408a-408b, each projection 404a-404b could include one or more holes of any suitable shape(s).

After the intraocular pseudophakic contact lens 400 is inserted into a patient's eye, a surgeon or other personnel could place the intraocular pseudophakic contact lens 400 onto an intraocular lens. Before, during, or after insertion of the intraocular pseudophakic contact lens 400, the surgeon or other personnel could insert the anchors 406a-406b through the holes 408a-408b of the intraocular pseudophakic contact lens 400. The surgeon or other personnel can push the anchors 406a-406b or other portion(s) of the intraocular pseudophakic contact lens 400 down onto the intraocular lens, which drives the anchors 406a-406b through the anterior surface of the intraocular lens and helps to secure the intraocular pseudophakic contact lens 400 to the intraocular lens.

Figure 8:
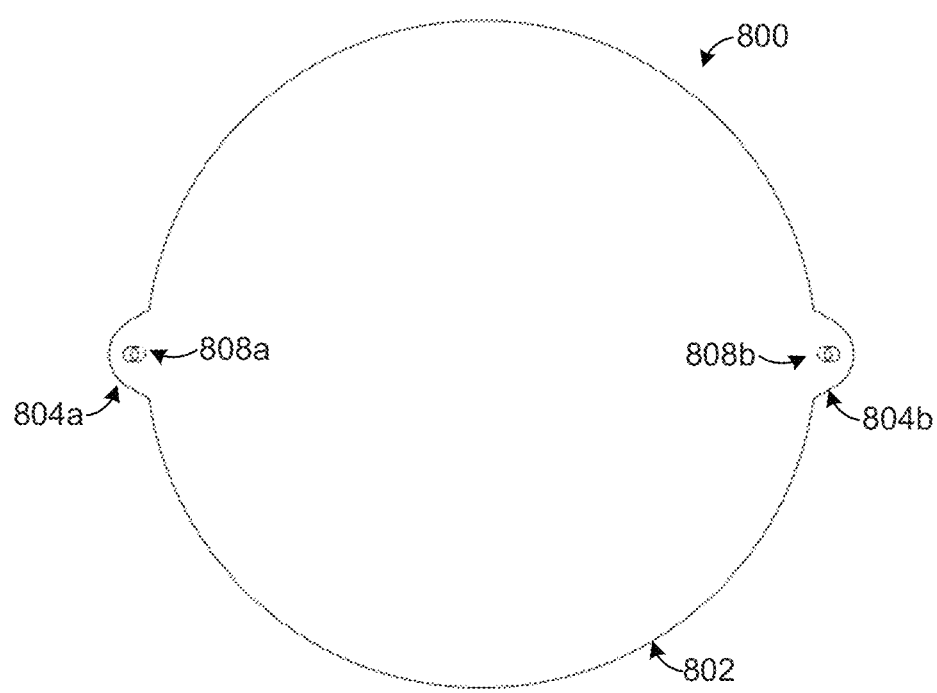
FIG. 8 illustrates a third example intraocular pseudophakic contact lens according to this disclosure.

FIG. 8 illustrates a third example intraocular pseudophakic contact lens 800 according to this disclosure. This embodiment of the intraocular pseudophakic contact lens 800 is similar in structure to the intraocular pseudophakic contact lens 400. The intraocular pseudophakic contact lens 800 includes an optical lens 802, projections 804a-804b, and holes 808a-808b configured to receive anchors. All of the discussion above regarding the optical lens 402, projections 404a-404b, and holes 408a-408b apply to the corresponding components in FIG. 8.

In this example, the holes 808a-808b are angled to a larger degree compared to the holes 408a-408b described above. The larger angle of the holes 808a-808b could be needed or desired in certain circumstances. For instance, the larger angle of the holes 808a-808b could be used to attach the intraocular pseudophakic contact lens 800 near the edge of an intraocular lens, where the anterior surface of the intraocular lens may be angled more.

While various prior approaches have secured an "add-on" lens to an intraocular lens, these prior approaches require a specific add-on lens to be designed for use with a specific intraocular lens and the specific intraocular lens to be designed for use with the specific add-on lens. That is, the add-on lens can only be used with a specific type of intraocular lens, where that intraocular lens is designed specifically for use with that add-on lens. As particular examples, an add-on lens may include haptics or other structures that are designed to mate with corresponding structures of specific intraocular lenses, or an intraocular lens may have a recess designed to receive a specific type of add-on lens. This can be problematic for a number of reasons. For instance, many patients already have existing intraocular lenses, and it may be impractical or even dangerous to try to remove those existing intraocular lenses in order to implant new intraocular lenses that are designed for use with add-on lenses.

The embodiments of the intraocular pseudophakic contact lenses 100, 400, 800 shown in FIGS. 1 through 8 can help to alleviate these problems since the anchors of the intraocular pseudophakic contact lenses are driven into the actual lens material forming an intraocular lens. In other words, the intraocular pseudophakic contact lens 100, 400, 800 need not be designed to work specifically with particular structures of any specific intraocular lens. Rather, the intraocular pseudophakic contact lens 100, 400, 800 can simply be sized so that, when the intraocular pseudophakic contact lens 100, 400, 800 is placed on an intraocular lens, its anchors can be driven into the lens material of the intraocular lens. This allows the intraocular pseudophakic contact lenses 100, 400, 800 to be used with a wide variety of intraocular lenses, including different types of intraocular lenses and including existing intraocular lenses already implanted into patients. There is no need to remove an existing intraocular lens from a patient in order to install a new intraocular lens and an intraocular pseudophakic contact lens.

Moreover, the anchors of an intraocular pseudophakic contact lens 100, 400, 800 could be easily removed from the lens material of an intraocular lens in order to remove the intraocular pseudophakic contact lens 100, 400, 800 from the intraocular lens. Among other things, this allows one intraocular pseudophakic contact lens to be removed and replaced with a different intraocular pseudophakic contact lens if a different refractive correction is needed or desired.

Figure 9:
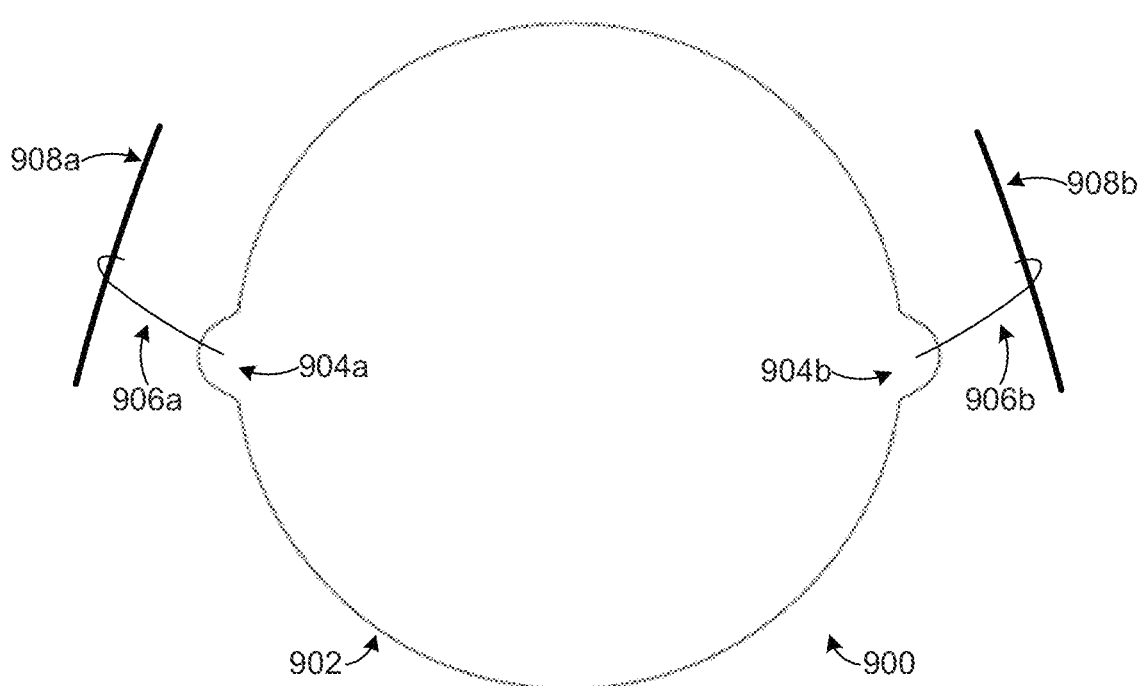
FIG. 9 illustrates a fourth example intraocular pseudophakic contact lens according to this disclosure.

FIG. 9 illustrates a fourth example intraocular pseudophakic contact lens 900 according to this disclosure. As shown in FIG. 9, the intraocular pseudophakic contact lens 900 includes an optical lens 902, which could be the same as or similar to the optical lenses described above. The intraocular pseudophakic contact lens 900 also includes projections 904a-904b, which could be the same as or similar to the projections described above.

Unlike the intraocular pseudophakic contact lenses described above, the projections 904a-904b here are coupled to haptic loops 906a-906b. The haptic loops 906a-906b are used to secure the intraocular pseudophakic contact lens 900 to portions 908a-908b of the capsular bag in a patient's eye. The haptic loops 906a-906b could be formed from any suitable material(s) and in any suitable manner. For example, the haptic loops 906a-906b could be formed from polyimide. Also, the haptic loops 906a-906b could have any suitable size, shape, and dimensions. As particular examples, the haptic loops 906a-906b could be about 2 mm to about 4 mm in length. Also, if desired, the haptic loops 906a-906b could have an angled down posture (such as an angle of about 3°), which can help to provide easier anchoring to the anterior capsule wall.

Note that while two projections and two haptic loops are shown here, the intraocular pseudophakic contact lens 900 could include any number of projections and haptic loops. Also, while not shown, a combination of haptic loops and anchors could be used in the intraocular pseudophakic contact lens 900. For instance, the projections 904a-904b could be coupled to the haptic loops 906a-906b, and anchors could be inserted into or embedded within the projections 904a-904b. As another example, one set of projections could be coupled to the haptic loops 906a-906b, and anchors could be inserted into or embedded within another set of projections.

Also note that while anchors and haptic loops are described above to couple an intraocular pseudophakic contact lens to an intraocular lens, any other suitable mechanisms could be used to attach an intraocular pseudophakic contact lens to an intraocular lens. For example, an intraocular pseudophakic contact lens could include an optical lens (with or without projections), and the intraocular pseudophakic contact lens could be held in place on an intraocular lens via surface tension with the anterior surface of the intraocular lens.

The various intraocular pseudophakic contact lenses described above could have any suitable size, shape, and dimensions. For example, the intraocular pseudophakic contact lenses could be made available in a range of diameters from about 4 mm to about 6 mm. Also, the intraocular pseudophakic contact lenses could be made available with varying base curvatures for their optical lenses. Of course, an intraocular pseudophakic contact lens could also be custom designed for a particular patient's eye, such as when one or more specific curvatures are needed to correct for residual refractive error in the particular patient's eye.

The intraocular pseudophakic contact lenses disclosed here can be implanted non-invasively in patients' eyes and easily positioned on intraocular lenses. The implantation is non-invasive because an intraocular pseudophakic contact lens is being installed on the anterior surface of an intraocular lens, which is typically easily accessible by a surgeon or other personnel during an implantation procedure. The implantation is also non-invasive because some of the intraocular pseudophakic contact lenses can be attached to intraocular lenses without requiring attachment of the intraocular pseudophakic contact lenses to anatomical structures within the patients' eyes, such as to the suculus of a patient's eye.

The non-invasive implantation and easy positioning of an intraocular pseudophakic contact lens provides a safe and effective refractive surgical procedure to correct unwanted residual refractive error, such as after a lensectomy procedure. As a refractive modality, the intraocular pseudophakic contact lenses contribute to a surgeon's ability to alter the current refractive error of a pseudophakic patient in an effort to adjust the patient's vision to achieve a finely-tuned desired refraction. Specific examples of this functionality include allowing adjustments to a patient's eye in order to achieve unilateral or bilateral emmetropia, to induce unilateral myopia to allow for intermediate and near visual function, to introduce multi-focality, and to treat unwanted residual astigmatism.

Although FIGS. 1 through 9 illustrate examples of intraocular pseudophakic contact lens, various changes may be made to FIGS. 1 through 9. For example, any combination of features shown in FIGS. 1 through 9 could be used in a single intraocular pseudophakic contact lens, whether or not that specific combination of features is shown in the figures or described above. Also, each intraocular pseudophakic contact lens could include any suitable number of each component shown in the figure(s). In addition, while anchors and haptic loops are shown as being used on projections from optical lenses, anchors and haptic loops could instead be used directly with the optical lenses (such as when the optical lenses are larger than needed in order to correct residual refractive errors).

Figure 10:
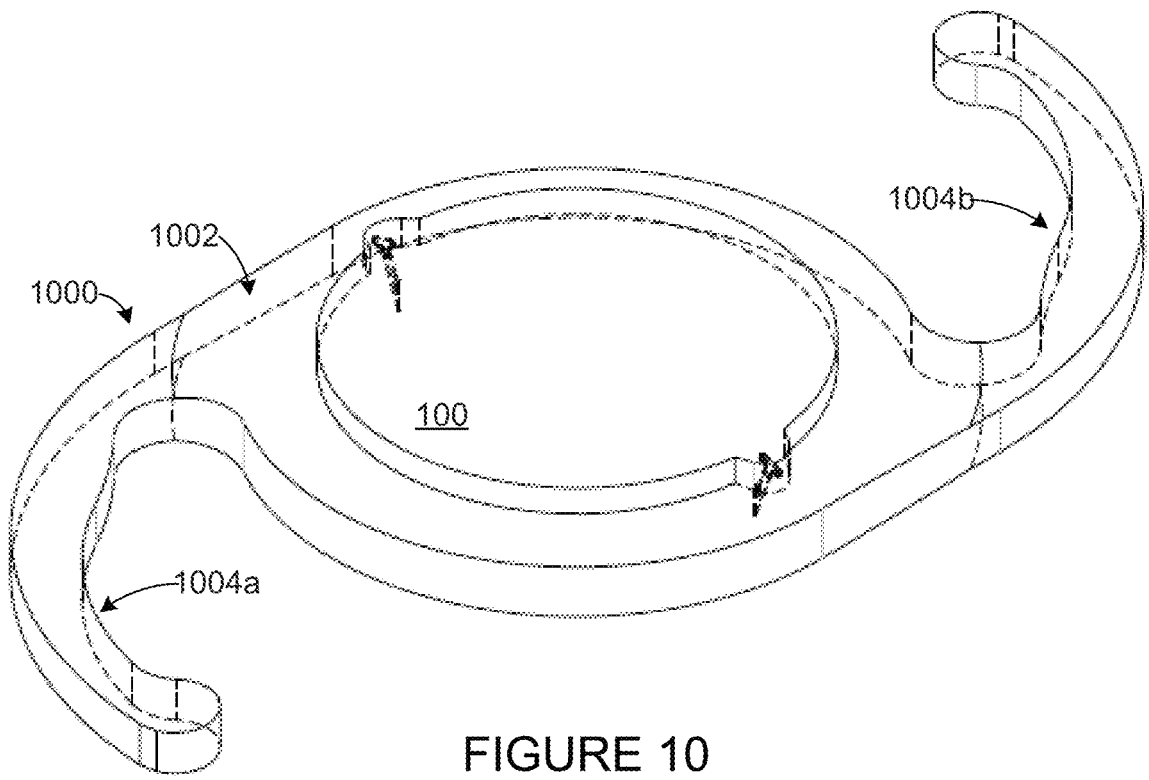
FIGS. 10 through 12 illustrate an example intraocular lens (IOL) attached to an example intraocular pseudophakic contact lens according to this disclosure.
Figure 11:
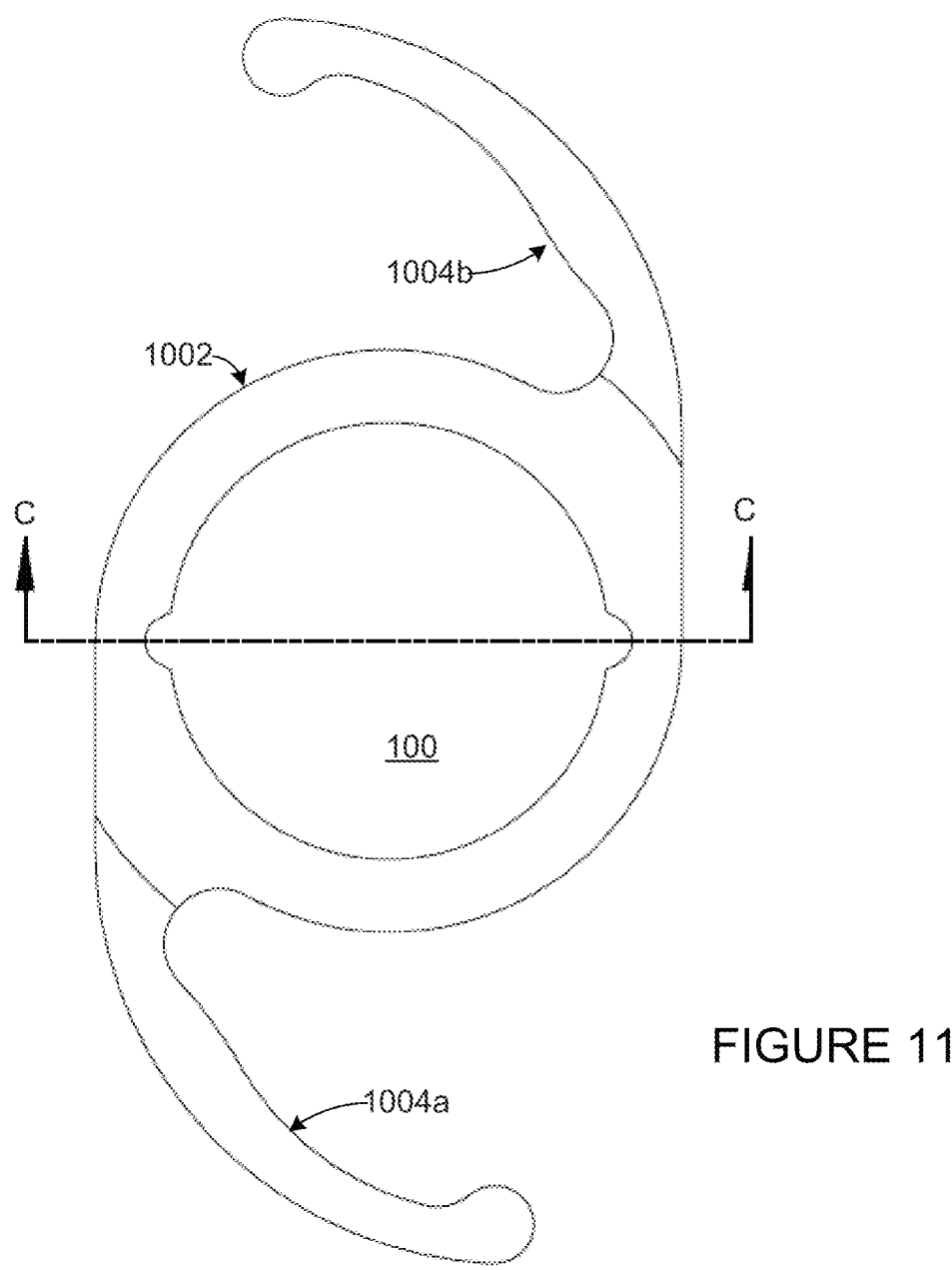
Figure 12:
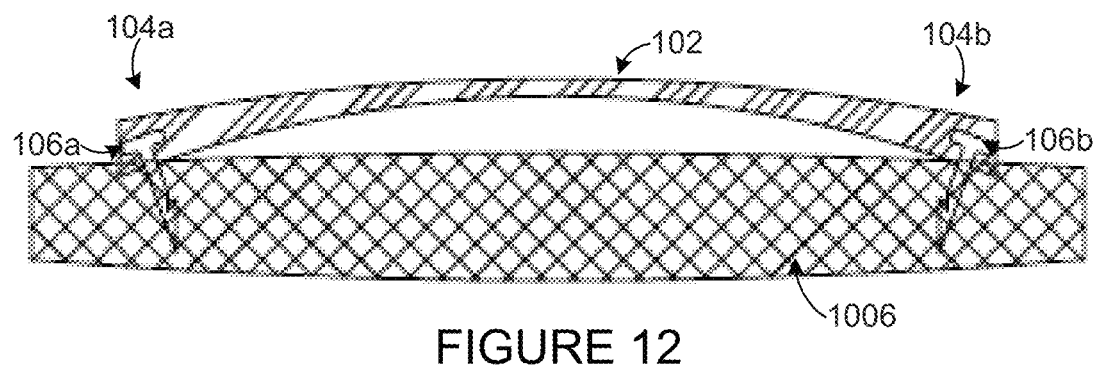

FIGS. 10 through 12 illustrate an example intraocular lens (IOL) 1000 attached to an example intraocular pseudophakic contact lens 100 according to this disclosure. In particular, FIG. 10 illustrates an oblique view of the system, FIG. 11 illustrates a top view of the system, and FIG. 12 illustrates a cut-away view of the system along line C-C in FIG. 11.

As shown in FIGS. 10 and 11, the intraocular lens 1000 includes an optical lens 1002 and multiple haptics 1004a-1004b. The optical lens 1002 receives light entering the eye (including light that passes through the intraocular pseudophakic contact lens 100) and focuses the light onto the retina of a patient's eye. The haptics 1004a-1004b help to hold the optical lens 1002 in a desired position within a patient's eye. For example, the entire intraocular lens 1000 could be placed within the capsular bag of a patient's eye, and the haptics 1004a-1004b could contact the inner walls of the capsular bag to hold the optical lens 1002 in the desired position.

As shown in FIGS. 10 through 12, the intraocular pseudophakic contact lens 100 has been placed on the intraocular lens 1000, and the anchors 106a-106b of the intraocular pseudophakic contact lens 100 have been driven through the anterior surface of the intraocular lens 1000 into lens material 1006 of the optical lens 1002. As noted above, this secures the intraocular pseudophakic contact lens 100 to the intraocular lens 1000. Moreover, this can be done without requiring the intraocular lens 1000 to be designed specifically for use with the intraocular pseudophakic contact lens 100 and without requiring the intraocular pseudophakic contact lens 100 to be designed specifically for use with the intraocular lens 1000.

This can be advantageous in various circumstances, such as when the intraocular lens 1000 has already been implanted into a patient's eye and cannot be removed without excessive surgical risks or cannot be removed at all (such as due to long-standing pseudophakia). Also, if the selected intraocular pseudophakic contact lens 100 does not remedy residual refractive error or if the intraocular pseudophakic contact lens 100 actually creates additional refractive error, the anchors 106a-106b can be extracted from the lens material 1006 in order to remove the intraocular pseudophakic contact lens 100 from the intraocular lens 1000. A different intraocular pseudophakic contact lens could then be placed on the intraocular lens 1000 in the same or similar manner.

Note that in FIG. 12, outer portions of the intraocular pseudophakic contact lens 100 are actually driven into the lens material 1006. However, this is not required. Moreover, in FIG. 12, only the outer portions of the intraocular pseudophakic contact lens 100 are contacting the lens material 1006, and the remaining lower surface of the optical lens 102 in the intraocular pseudophakic contact lens 100 is spaced apart from the lens material 1006. However, it is possible for more (or substantially all) of the lower surface of the optical lens 102 in the intraocular pseudophakic contact lens 100 to contact the lens material 1006.

Although FIGS. 10 through 12 illustrate one example of an intraocular lens attached to one example of an intraocular pseudophakic contact lens, various changes may be made to FIGS. 10 through 12. For example, the intraocular lens 1000 could be attached to any other intraocular pseudophakic contact lens, such as the contact lens 400 or 800 described above. Also, there are a number of intraocular lenses available, and the intraocular lens 1000 represents one specific type of intraocular lens. Intraocular pseudophakic contact lenses could be coupled to any other suitable intraocular lenses.

Figure 13:
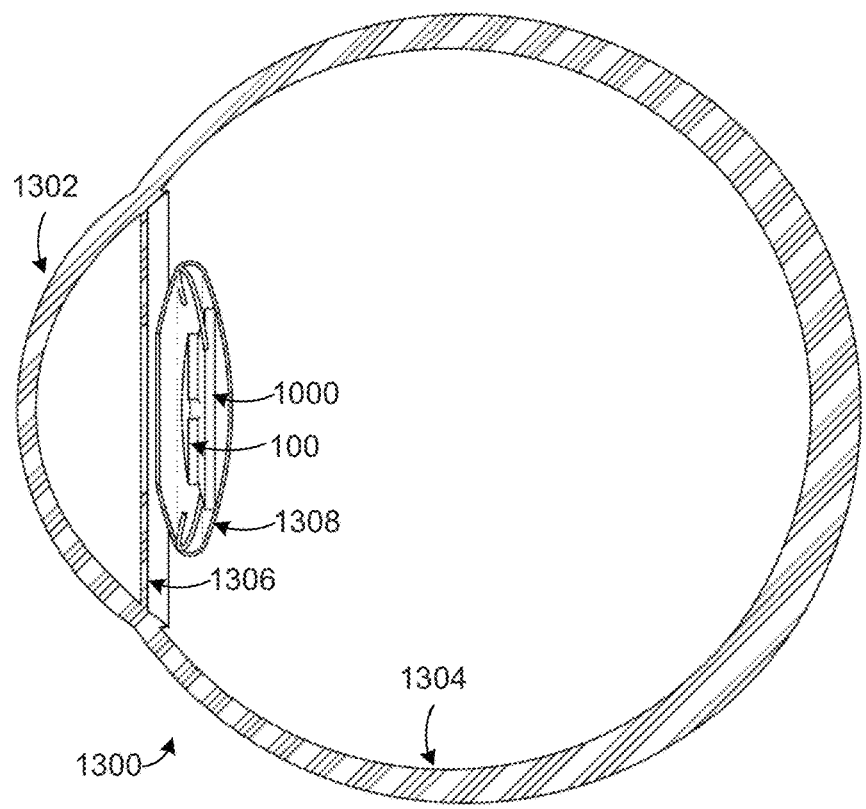
FIGS. 13 and 14 illustrate an example intraocular lens and an example intraocular pseudophakic contact lens in a patient's eye according to this disclosure.
Figure 14:
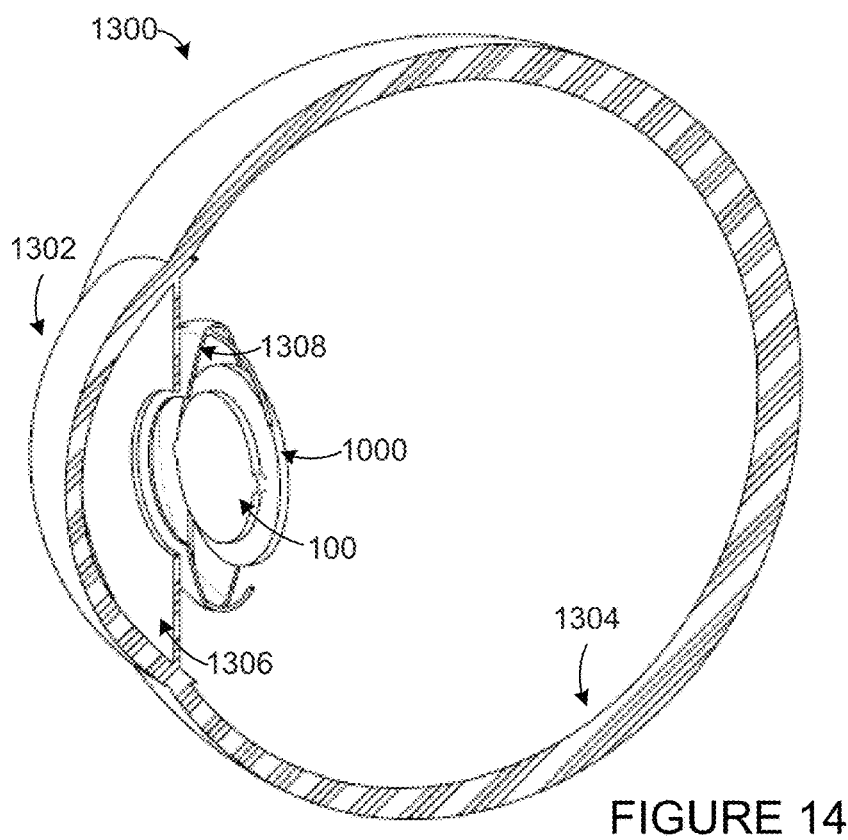

FIGS. 13 and 14 illustrate an example intraocular lens 1000 and an example intraocular pseudophakic contact lens 100 in a patient's eye 1300 according to this disclosure. As shown in FIGS. 13 and 14, the eye 1300 includes a cornea 1302, a sclera 1304, and an iris 1306. The cornea 1302 represents the clear front portion of the eye 1300 through which light passes to enter into the eye 1300. The sclera 1304 is the tough outer white portion of the eye. The iris 1306 controls the size of the eye's pupil to thereby control the amount of light from the cornea 1302 that enters into the interior of the eye 1300.

The eye 1300 also includes a capsular bag 1308, which typically holds the natural crystalline lens of the eye 1300. However, in this example, the natural crystalline lens has been removed and replaced with the intraocular lens 1000. The haptics 1004a-1004b of the intraocular lens 1000 help to hold the intraocular lens 1000 within the capsular bag 1308 so that the optical lens 1002 of the intraocular lens 1000 is in a desired position within the eye.

An intraocular pseudophakic contact lens 100 has also been placed on the intraocular lens 1000 within the capsular bag 1308. The intraocular pseudophakic contact lens 100 is placed on the anterior surface of the intraocular lens 1000, meaning the front surface of the intraocular lens 1000 with respect to the eye 1300. Light enters through the cornea 1302 and passes through the pupil before entering the intraocular pseudophakic contact lens 100, which modifies the light. The modified light then passes through the optical lens 1002 of the intraocular lens 1000 and is again modified. The twice-modified light then travels through the remainder of the eye 1300 to reach the retina at the back of the eye 1300.

By properly selecting the optical lens 102 of the intraocular pseudophakic contact lens 100, the intraocular pseudophakic contact lens 100 can ideally correct any residual refractive error that remains after implantation of the intraocular lens 1000. If necessary, the intraocular pseudophakic contact lens 100 can also be removed and replaced with a different intraocular pseudophakic contact lens if the intraocular pseudophakic contact lens 100 does not properly correct the residual refractive error or if the intraocular pseudophakic contact lens 100 actually causes additional refractive errors.

Although FIGS. 13 and 14 illustrate one example of an intraocular lens and one example of an intraocular pseudophakic contact lens in a patient's eye, various changes may be made to FIGS. 13 and 14. For example, the intraocular lens 1000 could be attached to any other intraocular pseudophakic contact lens, such as the contact lens 400 or 800 described above. Also, there are a number of intraocular lenses available, and an intraocular pseudophakic contact lens could be coupled to any other suitable intraocular lens in the eye 1300. In addition, some intraocular lenses need not reside within the capsular bag of an eye, in which case the intraocular pseudophakic contact lens would also not reside within the capsular bag of the eye.

Figure 15:
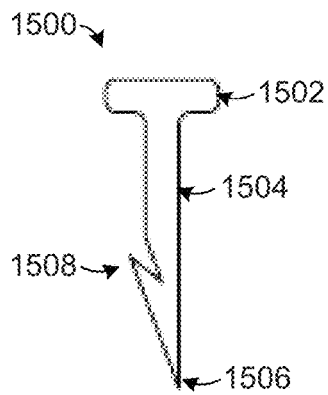
FIG. 15 illustrates an example anchor for attaching an intraocular pseudophakic contact lens to an intraocular lens according to this disclosure.

FIG. 15 illustrates an example anchor 1500 for attaching an intraocular pseudophakic contact lens to an intraocular lens according to this disclosure. The anchor 1500 could, for example, be used in conjunction with any of the intraocular pseudophakic contact lenses described above.

As shown in FIG. 15, the anchor 1500 includes a head 1502 and a shaft 1504. The head 1502 represents the top of the anchor 1500 and is larger than the shaft 1504, although this need not be the case depending on how the anchor 1500 is used (such as when the head 1502 is embedded in a projection). The shaft 1504 extends downward from the head 1502 to a sharp tip 1506. The tip 1506 is designed to be inserted into lens material of an intraocular lens. The shaft 1504 also includes a barbed or ribbed section 1508, which is designed to be inserted into the lens material of the intraocular lens and resist (but not necessarily prevent) removal of the shaft 1504 from the lens material of the intraocular lens. This helps to secure an intraocular pseudophakic contact lens to the lens material of the intraocular lens while still allowing removal of the intraocular pseudophakic contact lens from a patient's eye if needed or desired.

Although FIG. 15 illustrates one example of an anchor 1500 for attaching an intraocular pseudophakic contact lens to an intraocular lens, various changes may be made to FIG. 15. For example, an anchor could be used without any larger head or without any barbed or ribbed section. Also, any other suitable anchor(s) could be used to attach an intraocular pseudophakic contact lens to an intraocular lens.

FIGS. 16 through 24 illustrate example additional features that could be used with an intraocular pseudophakic contact lens according to this disclosure. None, one, or any suitable combination of these features could be used with an intraocular pseudophakic contact lens, including any of the intraocular pseudophakic contact lenses described above.

Figure 16:
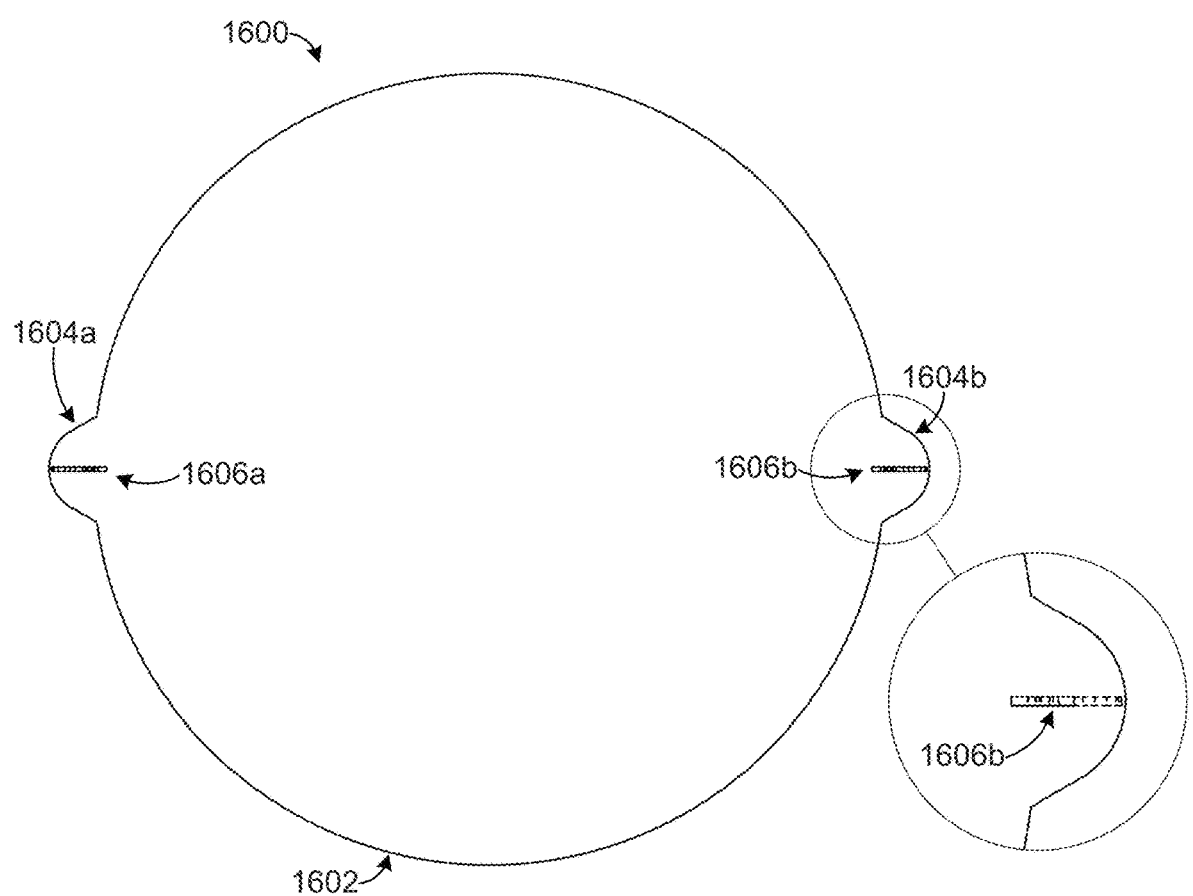
FIG. 16 illustrates example alignment markings that could be used with an intraocular pseudophakic contact lens according to this disclosure.

FIG. 16 illustrates a top view of an intraocular pseudophakic contact lens 1600 that includes an optical lens 1602 and projections 1604a-1604b, which may be the same as or similar to the corresponding components described above. While not shown, the intraocular pseudophakic contact lens 1600 also includes multiple holes configured to receive multiple anchors.

In addition, the intraocular pseudophakic contact lens 1600 includes alignment markings 1606a-1606b. The alignment markings 1606a-1606b generally identify the desired or optimal positioning of the anchors once inserted through the holes. For example, the optical lens 1602 and the projections 1604a-1604b could be substantially transparent, so anchors inserted into the projections 1604a-1604b and exiting underneath the intraocular pseudophakic contact lens 1600 could be visible from over the intraocular pseudophakic contact lens 1600. The alignment markings 1606a-1606b can be used by a surgeon or other personnel to help ensure that the anchors are being inserted straight into the underlying lens material of an intraocular lens, rather than being inserted crooked into the underlying lens material of the intraocular lens or even missing the lens material altogether. In addition, these markers 1606a-1606b can be used to identify the refractive correction (cylinder) in a toric application to allow the surgeon or other personnel to orientate the optical lens 1602 at a desired axis.

Figure 17:
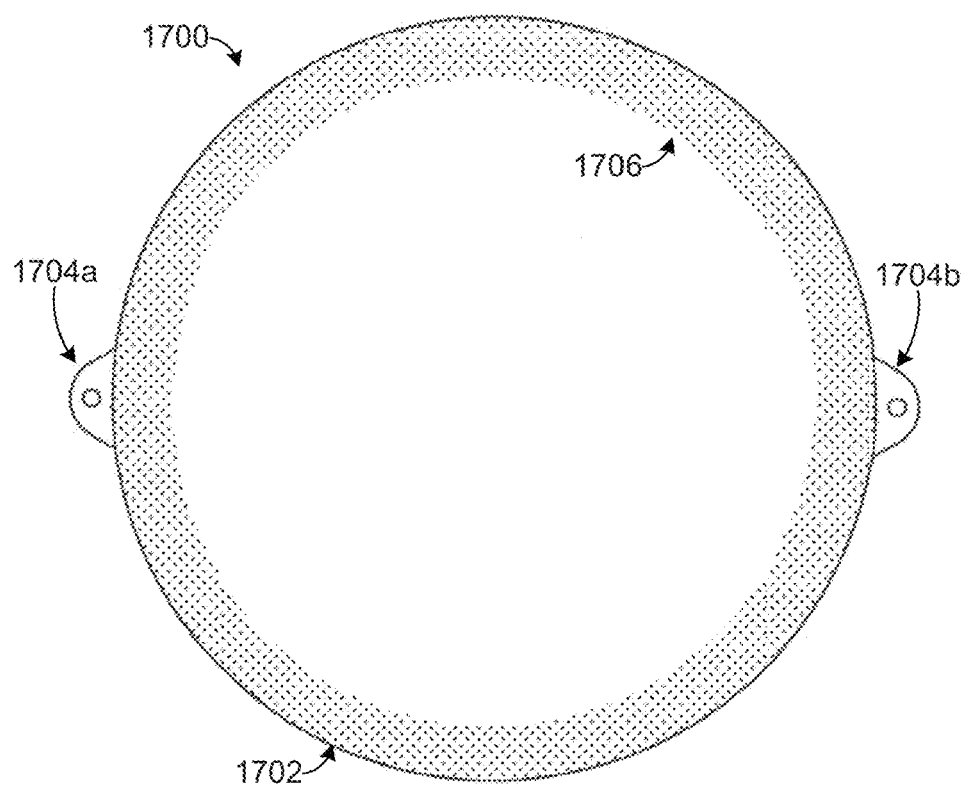
FIG. 17 illustrates an example drug-eluting matrix that could be used with an intraocular pseudophakic contact lens according to this disclosure.

FIG. 17 illustrates a top view of an intraocular pseudophakic contact lens 1700 that includes an optical lens 1702 and projections 1704a-1704b, which may be the same as or similar to the corresponding components described above. While the projections 1704a-1704b are shown as having holes configured to receive multiple anchors, this may not be required, such as when tops of the anchors are embedded in the projections 1704a-1704b.

The intraocular pseudophakic contact lens 1700 also includes a drug-eluting matrix 1706 formed on at least part of the optical lens 1702. The drug-eluting matrix 1706 in this example represents small areas where at least one medication has been deposited on the optical lens 1702, possibly within a gel or other mechanism that controls the release of the medication. Once implanted, the drug-eluting matrix 1706 releases the medication into a patient's eye.

Any suitable medication could be deposited on the optical lens 1702, such as (but not limited to) medication for treating glaucoma or uveitis. The deposition could have any suitable pattern and can be done in any suitable manner. For example, the medication could be deposited in an annular pattern, such as a ring about 0.5 mm thick, with an aperture or "donut hole" in the center of the pattern. Other depositions could be used, such as a "slit design" in the optical center of the optical lens 1702 allowing for enhanced vision with optical advantages (like increased depth of focus, cylinder reduction, or treatment of unwanted aberration).

Figure 18:
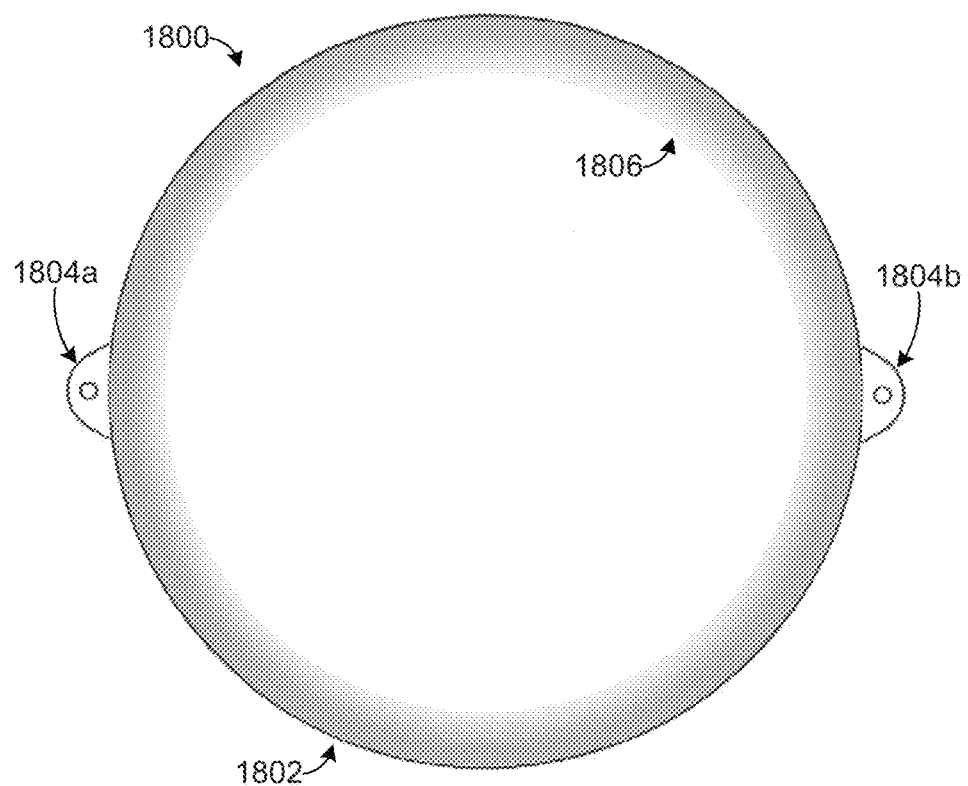
FIG. 18 illustrates an example drug-eluting film that could be used with an intraocular pseudophakic contact lens according to this disclosure.

FIG. 18 illustrates a top view of an intraocular pseudophakic contact lens 1800 that includes an optical lens 1802 and projections 1804a-1804b, which may be the same as or similar to the corresponding components described above. While the projections 1804a-1804b are shown as having holes configured to receive multiple anchors, this may not be required, such as when tops of the anchors are embedded in the projections 1804a-1804b.

The intraocular pseudophakic contact lens 1800 also includes a drug-eluting film 1806 formed on at least part of the optical lens 1802. The film 1806 in this example represents a continuous area where drug-eluting material that can deliver at least one medication has been deposited on the optical lens 1802. Any suitable medication could be deposited on the optical lens 1802, and the deposition could have any suitable pattern and can be done in any suitable manner. In this example, the medication is deposited in an annular pattern, such as a ring about 0.5 mm in thickness. Other depositions could be used, such as a "slit design" in the optical center of the optical lens 1802 allowing for enhanced vision with optical advantages. As a particular example, the film 1806 could represent a drug-eluting hydrogel.

Figure 19:
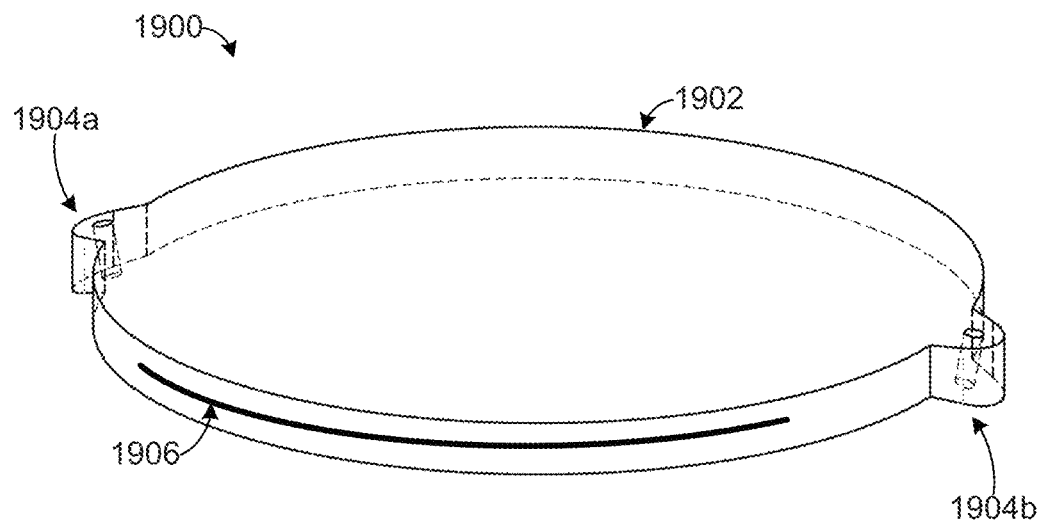
FIG. 19 illustrates an example drug-eluting ring that could be used with an intraocular pseudophakic contact lens according to this disclosure.

FIG. 19 illustrates an oblique view of an intraocular pseudophakic contact lens 1900 that includes an optical lens 1902 and projections 1904a-1904b, which may be the same as or similar to the corresponding components described above. While the projections 1904a-1904b are shown as having holes configured to receive multiple anchors, this may not be required, such as when tops of the anchors are embedded in the projections 1904a-1904b.

The intraocular pseudophakic contact lens 1900 also includes a drug-eluting ring 1906 formed along at least part of the edge of the optical lens 1902. The ring 1906 elutes at least one medication into a patient's eye once implanted. The ring 1906 may or may not be continuous around the entire optical lens 1902. In some embodiments, one or more rings 1906 could be used, where each ring is about 3 mm in length by about 0.5 mm in width. In particular embodiments, the ring 1906 could represent a polyimide or other reservoir formed along the edge of the optical lens 1902.

Note that FIGS. 17 through 19 have illustrated specific examples of drug-eluting structures for an intraocular pseudophakic contact lens. However, any other suitable type or types of drug-eluting structure(s) could be used at one or more locations of an intraocular pseudophakic contact lens.

Figure 20:
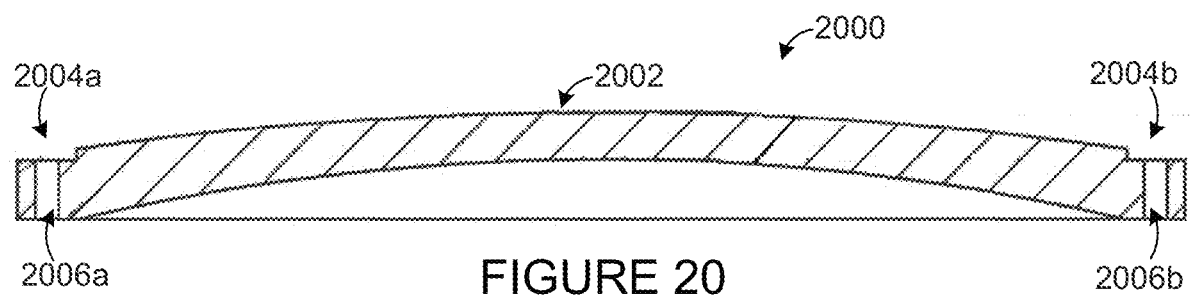
FIG. 20 illustrates an example intraocular pseudophakic contact lens having generally linear projections according to this disclosure.

FIG. 20 illustrates a cut-away view of an intraocular pseudophakic contact lens 2000 that includes an optical lens 2002, which may be the same as or similar to the corresponding components described above. Also, the intraocular pseudophakic contact lens 2000 includes multiple projections 2004a-2004b. In the examples described above, projections have extended away from an associated optical lens at opposing angles, which could allow for a natural opposing force that helps to ensure the forward permanent placement of anchors into the anterior surface of an intraocular lens. However, this may not be required, and the projections 2004a-2004b of the intraocular pseudophakic contact lens 2000 in FIG. 20 are generally linear with respect to one another. Holes 2006a-2006b through the projections 2004a-2004b could be formed straight up and down as shown in FIG. 20 or angled (such as in FIG. 19), which helps to direct the anchors inward toward a central axis of the optical lens 2002.

Figure 21A:
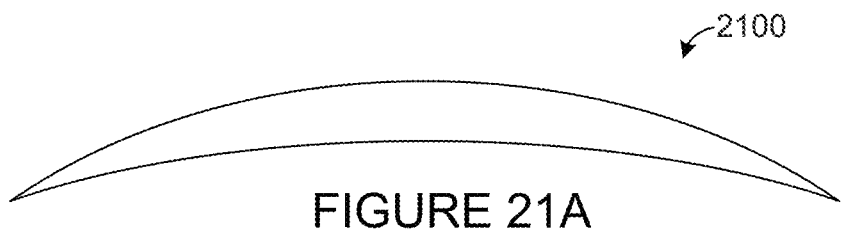
FIGS. 21A and 21B illustrate example optical lenses having varying thicknesses that could be used with an intraocular pseudophakic contact lens according to this disclosure.
Figure 21B:
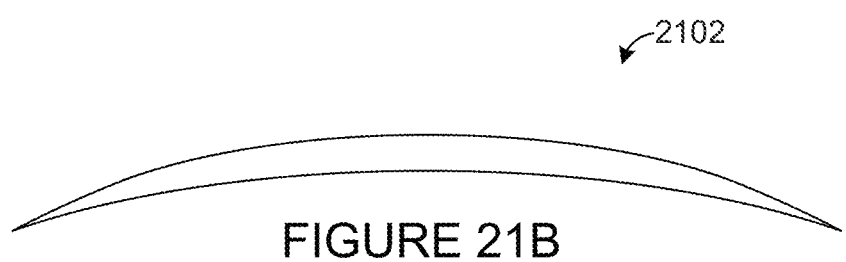

FIGS. 21A through 24 illustrate examples of various optical lenses that could be included in an intraocular pseudophakic contact lens. However, any other suitable optical lenses could be used in an intraocular pseudophakic contact lens. In FIGS. 21A and 21B, optical lenses 2100 and 2150 of varying thicknesses are shown. The optical lens 2100 has a larger central thickness and is generally spherical on both top and on bottom. The optical lens 2150 has a smaller central thickness and is somewhat flattened on top.

Figure 22A:
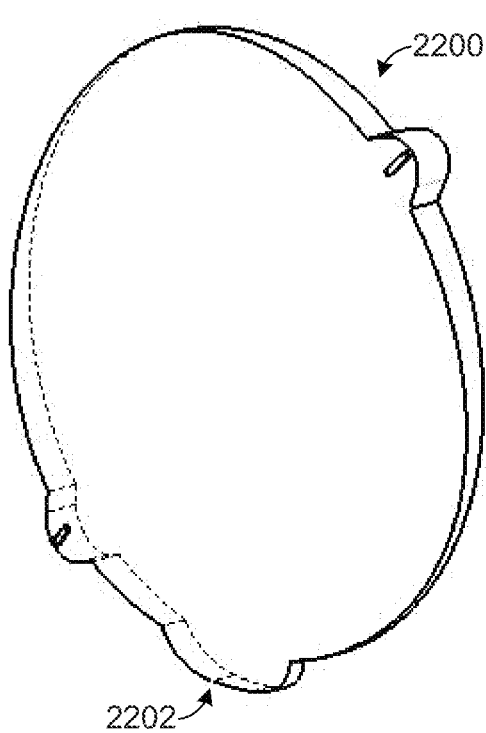
FIGS. 22A and 22B illustrate example optical lenses having uneven weight distributions that could be used with an intraocular pseudophakic contact lens according to this disclosure.
Figure 22B:
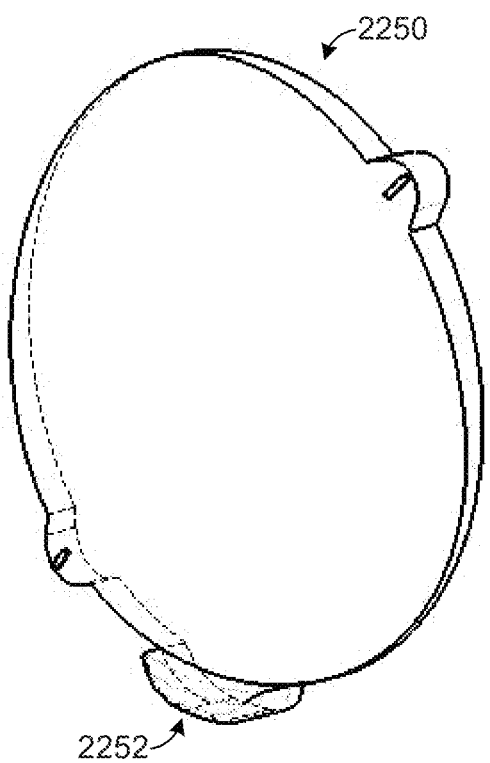

FIGS. 22A and 22B illustrate examples of optical lens 2200 and 2250 that include enlarged portions 2202 and 2252, respectively. The enlarged portions 2202 and 2252 have greater weights than other corresponding portions of the optical lenses 2200 and 2250, which causes the optical lenses 2200 and 2250 to move into the orientations shown in FIGS. 22A and 22B due to the larger weights of the enlarged portions 2202 and 2252. In other words, the optical lenses 2200 and 2250 have uneven weight distributions around central axes of the optical lenses 2200 and 2250. This can be useful, for example, when the optical lenses 2200 and 2250 are aspherical and need to have a particular orientation to correct a specific refractive error (such as astigmatism) in a patient's eye. The enlarged portions 2202 and 2252 could denote any enlarged portion of an optical lens, such as an enlarged edge of the optical lens in one quadrant of the optical lens.

In FIG. 22A, the enlarged portion 2202 has top and bottom surfaces generally even with top and bottom surfaces at an edge of the optical lens 2200. FIG. 22B shows a transparent image with the optic edge emphasized. Each of the enlarged portions 2202 and 2252 represents a weighted edge that allows the intraocular pseudophakic contact lens 2200 and 2250 to align a cylinder correction at a required axis, giving way to better stability and avoiding unwanted rotation.

Figure 23:
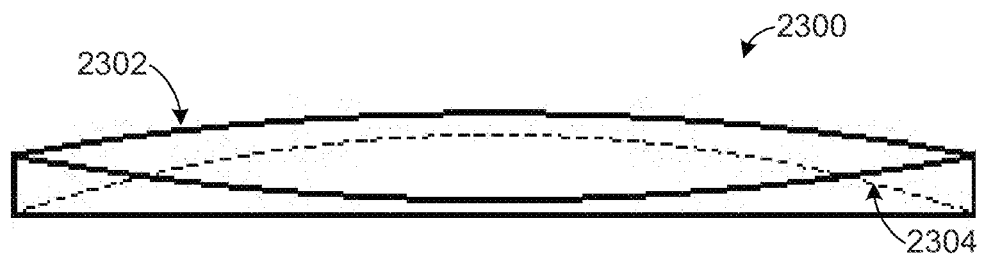
FIG. 23 illustrate an example optical lens having a toric shape that could be used with an intraocular pseudophakic contact lens according to this disclosure.

FIG. 23 illustrates an example optical lens 2300 in which the lens 2300 represents a tonic lens. A tonic lens refers to a lens having different optical powers and focal lengths in different perpendicular orientations. This can be seen in FIG. 23, where a top surface 2302 of the optical lens 2300 is curved in one direction (perpendicular to the figure) and a bottom surface 2304 of the optical lens 2300 is curved in a perpendicular direction (left-to-right in the figure).

Figure 24:
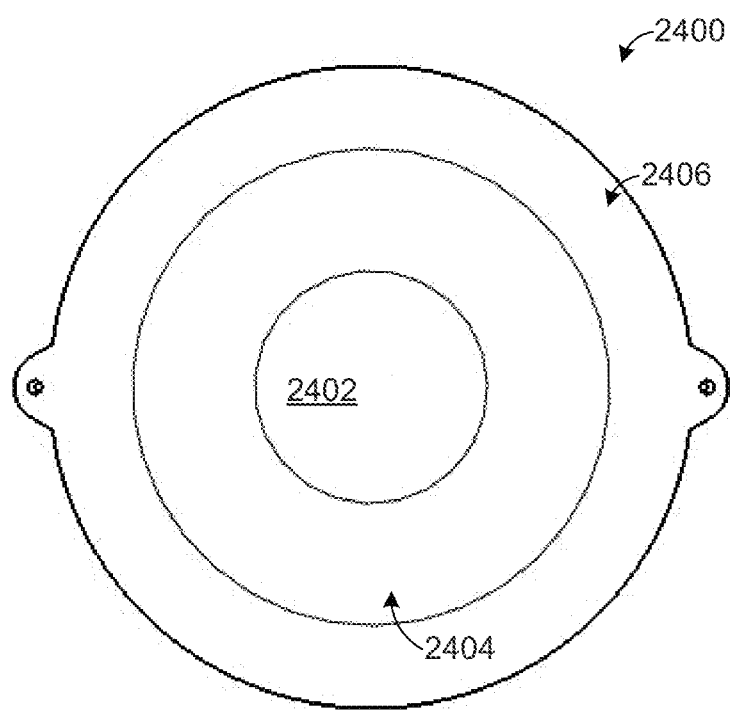
FIG. 24 illustrate an example optical lens having a nonspherical shape that could be used with an intraocular pseudophakic contact lens according to this disclosure.

FIG. 24 illustrates an example non-spherical optical lens 2400 supporting multi-focality. In FIG. 24, the optical lens 2400 includes a central region 2402 and one or more annular regions 2404-2406 that surround the spherical region 2402. Different regions 2402-2406 can be designed to provide different refractive powers. For example, some of the regions 2402-2406 could be designed for near vision, while others of the regions 2402-2406 could be designed for far vision.

In general, a wide variety of optical lenses can be used in intraocular pseudophakic contact lenses in order to provide desired refractive corrections for patients with residual refractive errors. One or more intraocular pseudophakic contact lenses for a specific patient could be selected or designed based on the type(s) of refractive correction needed in the patient's eye(s).

Although FIGS. 16 through 24 illustrate examples of additional features that could be used with an intraocular pseudophakic contact lens, various changes may be made to FIGS. 16 through 24. For example, each intraocular pseudophakic contact lens or optical lens could include any number of each feature shown for that intraocular pseudophakic contact lens or optical lens. Also, other or additional features could be used with the intraocular pseudophakic contact lenses described above.

Figure 25:
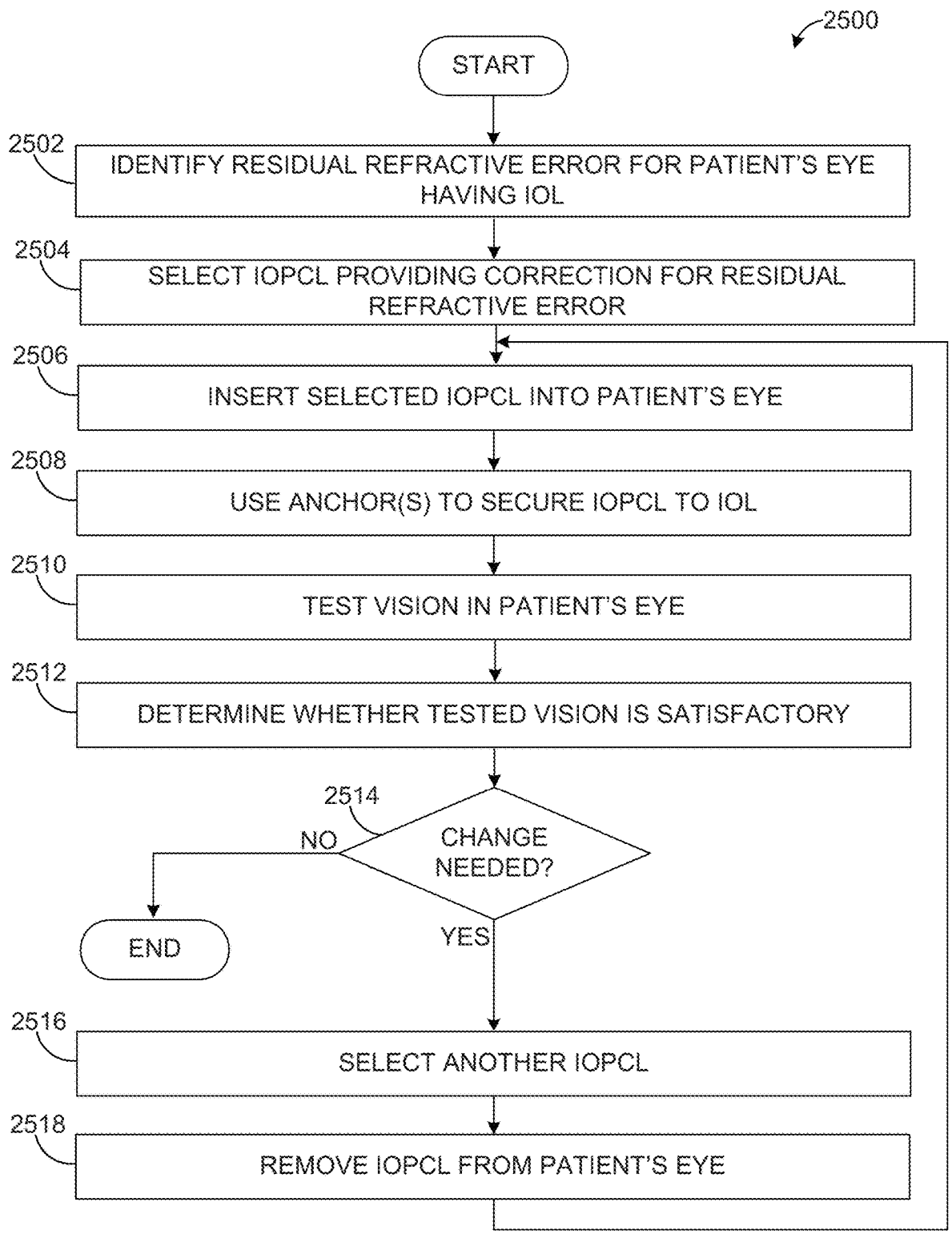
FIG. 25 illustrates an example method for using an intraocular pseudophakic contact lens with an intraocular lens according to this disclosure.

FIG. 25 illustrates an example method 2500 for using an intraocular pseudophakic contact lens with an intraocular lens according to this disclosure. As shown in FIG. 25, residual refractive error in a patient's eye having an intraocular lens is identified at step 2502. This could include, for example, personnel testing the patient's vision and identifying any refractive error that remains after implantation of the intraocular lens 1000. The testing could be done in any suitable manner, such as by using intraoperative wavefront aberrometry. One goal of the testing can be to identify what refractive errors exist in the patient's eye after implantation of the intraocular lens in the patient's eye. This testing could be performed at any suitable time, such as after a lensectomy procedure.

An intraocular pseudophakic contact lens is selected to (ideally) correct the identified residual refractive error at step 2504. This could include, for example, personnel selecting an intraocular pseudophakic contact lens from a kit, where the selected intraocular pseudophakic contact lens has an optical lens that substantially neutralizes the identified residual refractive error. This could also include the personnel selecting an optical lens from a kit and inserting the optical lens into an intraocular pseudophakic contact lens, where the selected optical lens substantially cancels the identified residual refractive error. This could further include the personnel obtaining an intraocular pseudophakic contact lens having a custom-designed optical lens or obtaining a custom-designed optical lens for insertion into an intraocular pseudophakic contact lens, where the custom-designed optical lens substantially cancels the identified residual refractive error. In general, any mechanism can be used to obtain a suitable intraocular pseudophakic contact lens.

The selected intraocular pseudophakic contact lens is inserted into the patient's eye at step 2506. This could include, for example, a surgeon or other personnel forming a small incision in the patient's eye and inserting the intraocular pseudophakic contact lens into the eye through the incision. The intraocular pseudophakic contact lens can be rolled, folded, or otherwise reduced in cross-sectional size in order to insert the intraocular pseudophakic contact lens through a smaller incision.

One or more anchors are used to secure the intraocular pseudophakic contact lens to an intraocular lens in the patient's eye at step 2508. This could include, for example, the surgeon or other personnel placing the intraocular pseudophakic contact lens at a desired position (and possibly in a desired orientation) on the intraocular lens. This could also include the surgeon or other personnel pushing down onto the intraocular pseudophakic contact lens or the anchors of the intraocular pseudophakic contact lens to push the anchors into the lens material of the intraocular lens in the patient's eye. This could further include placing haptic loops of the intraocular pseudophakic contact lens around portions of the capsular bag in the patient's eye.

A vision test for the patient occurs at step 2510. The vision test could be done in any suitable manner, such as by using intraoperative wavefront aberrometry. This vision test could also be performed at any suitable time, such as during the surgical procedure in which the intraocular pseudophakic contact lens is being implanted or after the surgical procedure has been completed. A determination is made whether the tested vision is satisfactory at step 2512. This could include, for example, personnel determining whether the patient's eye is still experiencing any residual refractive error and, if so, to what extent.

A determination is made whether to change the intraocular pseudophakic contact lens at step 2514. This could include, for example, the personnel and the patient determining whether the remaining residual refractive error (if any) is inconvenient or otherwise problematic for the patient. If so, different steps could be taken to try and fix the problem. For instance, the currently-implanted intraocular pseudophakic contact lens could be repositioned to adjust for cylinder axis correction. If that fails, another intraocular pseudophakic contact lens is selected at step 2516. This could include, for example, personnel selecting another intraocular pseudophakic contact lens that (ideally) provides a better refractive correction for the patient's eye compared to the currently-inserted intraocular pseudophakic contact lens. The currently-inserted intraocular pseudophakic contact lens is removed from the patient's eye at step 2518. This could include, for example, the surgeon or other personnel removing the anchors of the currently-inserted intraocular pseudophakic contact lens from the lens material of the intraocular lens and removing the currently-inserted intraocular pseudophakic contact lens from the patient's eye. The process then returns to step 2506, where the newly-selected intraocular pseudophakic contact lens can be inserted into the patient's eye and the vision test can be repeated.

Although FIG. 25 illustrates one example of a method 2500 for using an intraocular pseudophakic contact lens with an intraocular lens, various changes may be made to FIG. 25. For example, while shown as a series of steps, various steps in FIG. 25 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in this patent document should not be read as implying that any particular element, step, or function is an essential or critical element that must be included in the claim scope. Also, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
an intraocular pseudophakic contact lens comprising:
a first optical lens configured to at least partially correct a residual refractive error in an eye, the residual refractive error comprising a refractive error that exists in the eye after implantation of an artificial intraocular lens in the eye;
multiple anchors configured to be inserted through an anterior surface of the artificial intraocular lens into lens material forming a second optical lens of the artificial intraocular lens in order to secure the intraocular pseudophakic contact lens to the artificial intraocular lens; and
multiple projections comprising extensions of the first optical lens such that the first optical lens and the projections comprise a common material, the anchors partially embedded in or configured to pass through the extensions of the first optical lens, the projections substantially or completely coplanar with the first optical lens;
wherein the artificial intraocular lens lacks predefined openings that receive the anchors;

wherein the anchors are configured to pierce the lens material forming the second optical lens of the artificial intraocular lens in order to secure the intraocular pseudophakic contact lens to the artificial intraocular lens; and wherein the anchors comprise substantially straight pins extending axially along an optical axis of the intraocular pseudophakic contact lens away from the first optical lens.

2. The apparatus of claim 1, wherein the anchors are configured to couple the intraocular pseudophakic contact lens to different types of artificial intraocular lenses, including artificial intraocular lenses not specifically designed to be coupled to or receive the intraocular pseudophakic contact lens.

3. The apparatus of claim 1, further comprising:
at least one drug-eluting device located on the first optical lens and configured to deliver at least one medication.

4. The apparatus of claim 1, wherein the extensions of the first optical lens forming the projections extend away from the optical axis of the intraocular pseudophakic contact lens at opposing angles.

5. The apparatus of claim 1, wherein each anchor comprises a head that is embedded in one of the projections.

6. The apparatus of claim 1, wherein:
each of the projections comprises one or more holes; and
the anchors are configured to be inserted into and pass through the holes.

7. The apparatus of claim 1, wherein the pins comprise barbed or ribbed pins.

8. The apparatus of claim 1, wherein the first optical lens has an uneven weight distribution around a central axis of the first optical lens in order to cause the first optical lens to obtain a specified orientation with respect to the artificial intraocular lens.

9. The apparatus of claim 1, wherein the first optical lens is mono-focal or spherical.

10. The apparatus of claim 1, wherein the first optical lens is multi-focal or non-spherical.

11. The apparatus of claim 1, wherein the first optical lens is configured such that, when the anchors secure the intraocular pseudophakic contact lens to the artificial intraocular lens:
an outer portion of a surface of the first optical lens contacts the lens material of the second optical lens; and
a remaining portion of the surface of the first optical lens remains spaced apart from the lens material of the second optical lens.

12. A system comprising:
an intraocular pseudophakic contact lens comprising:
a first optical lens configured to at least partially correct a residual refractive error in an eye;
multiple anchors; and
multiple projections comprising extensions of the first optical lens such that the first optical lens and the projections comprise a common material, the anchors partially embedded in or configured to pass through the extensions of the first optical lens, the projections substantially or completely coplanar with the first optical lens; and
an artificial intraocular lens comprising a second optical lens, the second optical lens formed of lens material;
wherein the anchors are configured to be inserted through an anterior surface of the artificial intraocular lens into the lens material in order to secure the intraocular pseudophakic contact lens to the artificial intraocular lens;
wherein the artificial intraocular lens lacks predefined openings that receive the anchors;
wherein the anchors are configured to pierce the lens material forming the second optical lens of the artificial intraocular lens in order to secure the intraocular pseudophakic contact lens to the artificial intraocular lens; and
wherein the anchors comprise substantially straight pins extending axially along an optical axis of the intraocular pseudophakic contact lens away from the first optical lens.

13. The system of claim 12, wherein the artificial intraocular lens is not specifically designed to be coupled to or receive the intraocular pseudophakic contact lens.

14. The system of claim 12, further comprising:
at least one drug-eluting device located on the first optical lens and configured to deliver at least one medication.

15. The system of claim 12, wherein the anchors extend inward from the projections at opposing angles toward the optical axis of the intraocular pseudophakic contact lens and away from the first optical lens.

16. The system of claim 12, wherein:
each of the projections comprises one or more holes; and
the anchors are configured to be inserted into and pass through the holes.

17. The system of claim 16, wherein the first optical lens comprises alignment markings configured to identify optimal positions for insertion of the anchors into the lens material, the alignment markings and the anchors both visible during insertion of the anchors into the lens material.

18. The system of claim 12, wherein the first optical lens has an uneven weight distribution around a central axis of the first optical lens in order to cause the first optical lens to obtain a specified orientation with respect to the artificial intraocular lens.

19. The system of claim 12, wherein the first optical lens is configured such that, when the anchors secure the intraocular pseudophakic contact lens to the artificial intraocular lens:
an outer portion of a surface of the first optical lens contacts the lens material of the second optical lens; and
a remaining portion of the surface of the first optical lens remains spaced apart from the lens material of the second optical lens.

20. A method comprising:
coupling an intraocular pseudophakic contact lens to an artificial intraocular lens;
wherein the intraocular pseudophakic contact lens comprises:
a first optical lens configured to at least partially correct a residual refractive error in an eye;
multiple anchors; and
multiple projections comprising extensions of the first optical lens such that the first optical lens and the projections comprise a common material, the anchors partially embedded in or configured to pass through the extensions of the first optical lens, the projections substantially or completely coplanar with the first optical lens;
wherein coupling the intraocular pseudophakic contact lens to the artificial intraocular lens comprises inserting the multiple anchors through an anterior surface of the artificial intraocular lens into lens material forming a second optical lens of the artificial intraocular lens in order to secure the intraocular pseudophakic contact lens to the artificial intraocular lens;

wherein the artificial intraocular lens lacks predefined openings that receive the anchors;

wherein the anchors are configured to pierce the lens material forming the second optical lens of the artificial intraocular lens in order to secure the intraocular pseudophakic contact lens to the artificial intraocular lens; and wherein the anchors comprise substantially straight pins extending axially along an optical axis of the intraocular pseudophakic contact lens away from the first optical lens.

\* \* \* \* \*